(12) United States Patent
Lee et al.

(10) Patent No.: US 12,649,785 B2
(45) Date of Patent: Jun. 9, 2026

(54) CHIMERIC ANTIGEN RECEPTOR TARGETING BCMA AND USE THEREOF

(71) Applicants: NATIONAL CANCER CENTER, Goyang-si (KR); PROTANBIO INC., Seoul (KR)

(72) Inventors: Sangjin Lee, Paju-si (KR); Hyeonseok Eom, Seoul (KR); Eunjung Park, Seoul (KR); Bumkyu Choi, Paju-si (KR); Soyoun Ro, Incheon (KR); Seongwon Hong, Goyang-si (KR); Chungyong Han, Goyang-si (KR); Jeyoel Cho, Seoul (KR); Hyejin Sung, Seoul (KR); Siyoung Choi, Seoul (KR)

(73) Assignees: NATIONAL CANCER CENTER, Goyang-si (KR); PROTANBIO INC., Seoul (KR)

( * ) Notice: Subject to any disclaimer, the term of this patent is extended or adjusted under 35 U.S.C. 154(b) by 745 days.

(21) Appl. No.: 18/002,109

(22) PCT Filed: May 28, 2021

(86) PCT No.: PCT/KR2021/006671
§ 371 (c)(1),
(2) Date: Dec. 16, 2022

(87) PCT Pub. No.: WO2021/256724
PCT Pub. Date: Dec. 23, 2021

(65) Prior Publication Data
US 2023/0346835 A1 Nov. 2, 2023

(30) Foreign Application Priority Data
Jun. 17, 2020 (KR) ........................ 10-2020-0073714

(51) Int. Cl.
| | |
|---|---|
| *A61K 40/31* | (2025.01) |
| *A61K 40/11* | (2025.01) |
| *A61K 40/42* | (2025.01) |
| *C07K 16/28* | (2006.01) |
| *C12N 15/86* | (2006.01) |

(52) U.S. Cl.
CPC .............. *C07K 16/28* (2013.01); *A61K 40/11* (2025.01); *A61K 40/31* (2025.01); *A61K 40/4215* (2025.01); *C12N 15/86* (2013.01); *C07K 2317/53* (2013.01); *C07K 2317/565* (2013.01); *C12N 2740/15032* (2013.01); *C12N 2740/15041* (2013.01)

(58) Field of Classification Search
None
See application file for complete search history.

(56) References Cited

FOREIGN PATENT DOCUMENTS

| | | |
|---|---|---|
| KR | 10-2017-0037626 A | 4/2017 |
| KR | 10-2017-0135931 A | 12/2017 |
| KR | 10-2019-0015733 A | 2/2019 |
| KR | 10-2020-0039793 A | 4/2020 |

OTHER PUBLICATIONS

Feng, Deming et al., "Overview of anti-BCMA CAR-T immunotherapy for multiple myeloma and relapsed /refractory multiple myeloma," *Scandinavian Journal of Immunology*, May 29, 2020, vol. 92, No. 2, 11 pages.
International Search Report mailed on Aug. 27, 2021 in PCT/ KR2021/006671 filed on May 28, 2020 (5 pages).

*Primary Examiner* — Michail A Belyavskyi
(74) *Attorney, Agent, or Firm* — Oblon, McClelland, Maier & Neustadt, L.L.P.

(57) ABSTRACT

An antibody specifically binding to BCMA (B-cell maturation antigen) or fragment thereof, including: a heavy chain variable region including a CDR1 region represented by the amino acid sequence of SEQ ID NO: 1, a CDR2 region represented by the amino acid sequence of SEQ ID NO: 2, and a CDR3 region represented by the amino acid sequence of SEQ ID NO: 3; and a light chain variable region including a CDR1 region represented by the amino acid sequence of SEQ ID NO: 4, a CDR2 region represented by the amino acid sequence of SEQ ID NO: 5, and a CDR3 region represented by the amino acid sequence of SEQ ID NO: 6.

14 Claims, 6 Drawing Sheets
Specification includes a Sequence Listing.

hBCMA CAR-T culture

Binding assay

SEQUENCE LISTING

<160> NUMBER OF SEQ ID NOS: 32

<210> SEQ ID NO 1
<211> LENGTH: 8
<212> TYPE: PRT
<213> ORGANISM: Artificial
<220> FEATURE:
<223> OTHER INFORMATION: 3G4_VH_CDR1

<400> SEQUENCE: 1

Gly Tyr Thr Phe Thr Ser Tyr Val
1               5

<210> SEQ ID NO 2
<211> LENGTH: 8
<212> TYPE: PRT
<213> ORGANISM: Artificial
<220> FEATURE:
<223> OTHER INFORMATION: 3G4_VH_CDR2

<400> SEQUENCE: 2

Ile Ile Pro Tyr Asn Asp Gly Thr
1               5

<210> SEQ ID NO 3
<211> LENGTH: 11
<212> TYPE: PRT
<213> ORGANISM: Artificial
<220> FEATURE:
<223> OTHER INFORMATION: 3G4_VH_CDR3

<400> SEQUENCE: 3

Ala Arg Trp Asn Trp Asp Gly Tyr Phe Asp Val
1               5                   10

<210> SEQ ID NO 4
<211> LENGTH: 11
<212> TYPE: PRT
<213> ORGANISM: Artificial
<220> FEATURE:
<223> OTHER INFORMATION: 3G4_VL_CDR1

<400> SEQUENCE: 4

Lys Ser Leu Leu His Ser Asn Gly Ile Thr Tyr
1               5                   10

<210> SEQ ID NO 5
<211> LENGTH: 3
<212> TYPE: PRT
<213> ORGANISM: Artificial
<220> FEATURE:
<223> OTHER INFORMATION: 3G4_VL_CDR2

<400> SEQUENCE: 5

Gln Met Ser
1

<210> SEQ ID NO 6
<211> LENGTH: 9
<212> TYPE: PRT
<213> ORGANISM: Artificial
<220> FEATURE:
<223> OTHER INFORMATION: 3G4_VL_CDR3

<400> SEQUENCE: 6

Thr Gln Asn Leu Glu Leu Pro Phe Thr
1               5

<210> SEQ ID NO 7
<211> LENGTH: 118
<212> TYPE: PRT
<213> ORGANISM: Artificial
<220> FEATURE:
<223> OTHER INFORMATION: 3G4_VH chain

<400> SEQUENCE: 7

Gln Val Gln Leu Lys Glu Ser Gly Pro Glu Leu Val Lys Pro Gly Ala
1               5                   10                  15

Ser Val Lys Met Ser Cys Lys Ala Ser Gly Tyr Thr Phe Thr Ser Tyr
                20                  25                  30

Val Met His Trp Val Lys Gln Lys Pro Gly Gln Gly Leu Glu Trp Ile
            35                  40                  45

Gly Tyr Ile Ile Pro Tyr Asn Asp Gly Thr Lys Tyr Asn Glu Lys Phe
        50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Leu Tyr Tyr Cys
                85                  90                  95

Ala Arg Trp Asn Trp Asp Gly Tyr Phe Asp Val Trp Gly Ala Gly Thr
            100                 105                 110

Thr Val Thr Val Ser Ser
        115

<210> SEQ ID NO 8
<211> LENGTH: 112
<212> TYPE: PRT
<213> ORGANISM: Artificial
<220> FEATURE:
<223> OTHER INFORMATION: 3G4_VL chain

<400> SEQUENCE: 8

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
        50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Phe Tyr Cys Thr Gln Asn
                85                  90                  95

Leu Glu Leu Pro Phe Thr Phe Gly Ser Gly Thr Lys Leu Glu Ile Lys
            100                 105                 110

<210> SEQ ID NO 9
<211> LENGTH: 354
<212> TYPE: DNA
<213> ORGANISM: Artificial
<220> FEATURE:
<223> OTHER INFORMATION: 3G4_VH chain

<400> SEQUENCE: 9
caggtgcagc tgaaggagtc tggacctgag ctggtaaagc ctgggggcttc agtgaagatg      60 tcctgcaagg cttctggata cacattcact agctatgtta tgcactgggt gaagcagaag     120

-continued

```
cctgggcagg gccttgagtg gattggatat attattcctt acaatgatgg tactaagtac        180
aatgagaagt tcaaaggcaa ggccacactg acttcagaca atcctccag  tacagcctac        240 atggagctca gcagcctgac ctctgaggac tctgcgctct attactgtgc aagatggaac        300
tgggacgggg acttcgatgt ctggggcgca gggaccacgg tcaccgtctc ctca             354

<210> SEQ ID NO 10
<211> LENGTH: 336
<212> TYPE: DNA
<213> ORGANISM: Artificial
<220> FEATURE:
<223> OTHER INFORMATION: 3G4_VL chain

<400> SEQUENCE: 10
gatattgtga tgacgcaggc tgcattctcc aatccagtca ctcttggaac atcagcttcc         60
atctcctgca ggtctagtaa gagtctccta catagtaatg gcatcactta tttgtattgg        120
tatctgcaga agccaggcca gtctcctcag ctcctgattt atcagatgtc caaccttgcc        180
tcaggagtcc cagacaggtt cagtagcagt gggtcaggaa ctgatttcac actgagaatc        240
agcagagtgg aggctgagga tgtgggtgtt ttttactgta ctcaaaatct agaacttcca        300
ttcacgttcg gctcggggac aaagttggaa ataaaa                                  336

<210> SEQ ID NO 11
<211> LENGTH: 245
<212> TYPE: PRT
<213> ORGANISM: Artificial
<220> FEATURE:
<223> OTHER INFORMATION: 3G4_scFv

<400> SEQUENCE: 11

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Phe Tyr Cys Thr Gln Asn
                85                  90                  95

Leu Glu Leu Pro Phe Thr Phe Gly Ser Gly Thr Lys Leu Glu Ile Lys
            100                 105                 110

Gly Gly Gly Gly Ser Gly Gly Gly Gly Ser Gly Gly Gly Gly Ser Gln
        115                 120                 125

Val Gln Leu Lys Glu Ser Gly Pro Glu Leu Val Lys Pro Gly Ala Ser
    130                 135                 140

Val Lys Met Ser Cys Lys Ala Ser Gly Tyr Thr Phe Thr Ser Tyr Val
145                 150                 155                 160

Met His Trp Val Lys Gln Lys Pro Gly Gln Gly Leu Glu Trp Ile Gly
                165                 170                 175

Tyr Ile Ile Pro Tyr Asn Asp Gly Thr Lys Tyr Asn Glu Lys Phe Lys
            180                 185                 190

Gly Lys Ala Thr Leu Thr Ser Asp Lys Ser Ser Ser Thr Ala Tyr Met
        195                 200                 205
```

```
Glu Leu Ser Ser Leu Thr Ser Glu Asp Ser Ala Leu Tyr Tyr Cys Ala
    210             215             220
```

```
Arg Trp Asn Trp Asp Gly Tyr Phe Asp Val Trp Gly Ala Gly Thr Thr
225             230             235             240
```

```
Val Thr Val Ser Ser
            245
```

```
<210> SEQ ID NO 12
<211> LENGTH: 735
<212> TYPE: DNA
<213> ORGANISM: Artificial
<220> FEATURE:
<223> OTHER INFORMATION: 3G4_scFv
```

```
<400> SEQUENCE: 12
```

```
gatattgtga tgacgcaggc tgcattctcc aatccagtca ctcttggaac atcagcttcc         60
atctcctgca ggtctagtaa gagtctccta catagtaatg gcatcactta tttgtattgg        120
tatctgcaga agccaggcca gtctcctcag ctcctgattt atcagatgtc caaccttgcc        180
tcaggagtcc cagacaggtt cagtagcagt gggtcaggaa ctgatttcac actgagaatc        240
agcagagtgg aggctgagga tgtgggtgtt ttttactgta ctcaaaatct agaacttcca        300
ttcacgttcg gctcggggac aaagttggaa ataaaaggtg gtggtggttc gggtggtggt        360
ggttcgggtg tggtggttc gcaggtgcag ctgaaggagt ctggacctga ctggtaaag         420 cctggggctt cagtgaagat gtcctgcaag gcttctggat acacattcac tagctatgtt        480
atgcactggg tgaagcagaa gcctgggcag ggccttgagt ggattggata tattattcct        540
tacaatgatg gtactaagta caatgagaag ttcaaaggca aggccacact gacttcagac        600
aaatcctcca gtacagccta catggagctc agcagcctga cctctgagga ctctgcgctc        660
tattactgtg caagatggaa ctgggacggg tacttcgatg tctggggcgc agggaccacg        720
gtcaccgtct cctca                                                        735
```

```
<210> SEQ ID NO 13
<211> LENGTH: 118
<212> TYPE: PRT
<213> ORGANISM: Artificial
<220> FEATURE:
<223> OTHER INFORMATION: 3G4V2_VH chain
```

```
<400> SEQUENCE: 13
```

```
Gln Val Gln Leu Val Gln Ser Gly Ala Glu Val Lys Lys Pro Gly Ala
1               5               10              15
```

```
Ser Val Lys Val Ser Cys Lys Ala Ser Gly Tyr Thr Phe Thr Ser Tyr
                20              25              30
```

```
Val Met His Trp Val Arg Gln Ala Pro Gly Gln Arg Leu Glu Trp Ile
            35              40              45
```

```
Gly Tyr Ile Ile Pro Tyr Asn Asp Gly Thr Lys Tyr Asn Glu Lys Phe
        50              55              60
```

```
Gln Gly Arg Val Thr Leu Thr Ser Asp Lys Ser Ser Ser Thr Ala Tyr
65              70              75              80
```

```
Met Glu Leu Ser Ser Leu Arg Ser Glu Asp Thr Ala Val Tyr Tyr Cys
                85              90              95
```

```
Ala Arg Trp Asn Trp Asp Gly Tyr Phe Asp Val Trp Gly Gln Gly Thr
            100             105             110
```

```
Thr Val Thr Val Ser Ser
        115
```

```
<210> SEQ ID NO 14
<211> LENGTH: 112
<212> TYPE: PRT
<213> ORGANISM: Artificial
<220> FEATURE:
<223> OTHER INFORMATION: 3G4V2_VL chain

<400> SEQUENCE: 14

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Asn
                85                  90                  95

Leu Glu Leu Pro Phe Thr Phe Gly Gln Gly Thr Lys Leu Glu Ile Lys
            100                 105                 110

<210> SEQ ID NO 15
<211> LENGTH: 354
<212> TYPE: DNA
<213> ORGANISM: Artificial
<220> FEATURE:
<223> OTHER INFORMATION: 3G4V2_VH chain

<400> SEQUENCE: 15
caggtgcagc tggtgcagag cggcgccgag gtgaagaagc cgggtgcttc cgtgaaggtg      60
tcctgtaagg cctctggcta caccttcacc agctacgtga tgcattgggt ccgccaggcc     120
cccggacagc gcctggagtg gatcggttac atcatcccgt acaacgacgg cactaagtac     180
aacgagaaat tcagggccg agtgacctg acctccgaca atccagctc gaccgcctac      240 atggagctgt cttctctgcg ctcggaggac accgcggttt attactgtgc tcgttggaac     300
tgggatggct atttcgacgt gtggggccag ggaacgaccg tcaccgtgtc gtcc           354

<210> SEQ ID NO 16
<211> LENGTH: 336
<212> TYPE: DNA
<213> ORGANISM: Artificial
<220> FEATURE:
<223> OTHER INFORMATION: 3G4V2_VL chain

<400> SEQUENCE: 16
gacatcgtga tgacccagag ccctttgtct cttcctgtca ctccggggga gccagcttct      60
atctcatgcc gatcttccaa gagcctgctg cactcaaatg gcatcaccta cctctattgg     120
tacctgcaga gcccgggca atcccctcag ttgctcatct atcagatgtc taaccgcgcc     180
tccggtgtcc ccgaccgctt cagctcctct ggctccggca ccgactttac tctgaagata     240
tcccgcgtgg aggccgaaga tgtgggcgtg tactactgca ctcagaacct ggaactgccc     300
ttcaccttcg gccagggcac caagctggag atcaag                                336

<210> SEQ ID NO 17
<211> LENGTH: 245
```

<212> TYPE: PRT
<213> ORGANISM: Artificial
<220> FEATURE:
<223> OTHER INFORMATION: 3G4V2_scFv

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Thr Gln Asn
                85                  90                  95

Leu Glu Leu Pro Phe Thr Phe Gly Gln Gly Thr Lys Leu Glu Ile Lys
            100                 105                 110

Gly Gly Gly Gly Ser Gly Gly Gly Gly Ser Gly Gly Gly Gly Ser Gln
        115                 120                 125

Val Gln Leu Val Gln Ser Gly Ala Glu Val Lys Lys Pro Gly Ala Ser
    130                 135                 140

Val Lys Val Ser Cys Lys Ala Ser Gly Tyr Thr Phe Thr Ser Tyr Val
145                 150                 155                 160

Met His Trp Val Arg Gln Ala Pro Gly Gln Arg Leu Glu Trp Ile Gly
                165                 170                 175

Tyr Ile Ile Pro Tyr Asn Asp Gly Thr Lys Tyr Asn Glu Lys Phe Gln
            180                 185                 190

Gly Arg Val Thr Leu Thr Ser Asp Lys Ser Ser Ser Thr Ala Tyr Met
        195                 200                 205

Glu Leu Ser Ser Leu Arg Ser Glu Asp Thr Ala Val Tyr Tyr Cys Ala
    210                 215                 220

Arg Trp Asn Trp Asp Gly Tyr Phe Asp Val Trp Gly Gln Gly Thr Thr
225                 230                 235                 240

Val Thr Val Ser Ser
                245

<210> SEQ ID NO 18
<211> LENGTH: 735
<212> TYPE: DNA
<213> ORGANISM: Artificial
<220> FEATURE:
<223> OTHER INFORMATION: 3G4V2_scFv

<400> SEQUENCE: 18
gacatcgtga tgacccagag ccctttgtct cttcctgtca ctccggggga gccagcttct      60
atctcatgcc gatcttccaa gagcctgctg cactcaaatg gcatcaccta cctctattgg     120
tacctgcaga agcccgggca atcccctcag ttgctcatct atcagatgtc taaccgcgcc     180
tccggtgtcc ccgaccgctt cagctcctct ggctccggca ccgactttac tctgaagata     240
tcccgcgtgg aggccgaaga tgtgggcgtg tactactgca ctcagaacct ggaactgccc     300
ttcaccttcg gccagggcac caagctggag atcaagggcg gtggtggctc cggcggaggg     360
ggttctggag gcggcggctc ccaggtgcag ctggtgcaga gcggcgccga ggtgaagaag     420

```
ccgggtgctt ccgtgaaggt gtcctgtaag gcctctggct acaccttcac cagctacgtg      480
atgcattggg tccgccaggc ccccggacag cgcctggagt ggatcggtta catcatcccg      540
tacaacgacg gcactaagta caacgagaaa tttcagggcc gagtgaccct gacctccgac      600
aaatccagct cgaccgccta catggagctg tcttctctgc gctcggagga caccgcggtt      660
tattactgtg ctcgttggaa ctgggatggc tatttcgacg tgtggggcca gggaacgacc      720
gtcaccgtgt cgtcc                                                        735
```

```
<210> SEQ ID NO 19
<211> LENGTH: 54
<212> TYPE: PRT
<213> ORGANISM: Artificial
<220> FEATURE:
<223> OTHER INFORMATION: BCMA peptide

<400> SEQUENCE: 19

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala
    50
```

```
<210> SEQ ID NO 20
<211> LENGTH: 1178
<212> TYPE: DNA
<213> ORGANISM: Artificial
<220> FEATURE:
<223> OTHER INFORMATION: EF1 promoter

<400> SEQUENCE: 20
gctccggtgc ccgtcagtgg gcagagcgca catcgcccac agtccccgag aagttggggg       60
gaggggtcgg caattgaacc ggtgcctaga gaaggtggcg cggggtaaac tgggaaagtg      120
atgtcgtgta ctggctccgc cttttttccg agggtggggg agaaccgtat ataagtgcag      180
tagtcgccgt gaacgttctt tttcgcaacg ggtttgccgc cagaacacag gtaagtgccg      240
tgtgtggttc ccgcgggcct ggcctcttta cgggttatgg cccttgcgtg ccttgaatta      300
cttccacctg gctgcagtac gtgattcttg atcccgagct tcgggttgga agtgggtggg      360
agagttcgag gccttgcgct taaggagccc cttcgcctcg tgcttgagtt gaggcctggc      420
ctgggcgctg gggccgccgc gtgcgaatct ggtggcacct tcgcgcctgt ctcgctgctt      480
tcgataagtc tctagccatt taaaattttt gatgacctgc tgcgacgctt ttttctggc      540 aagatagtct tgtaaatgcg ggccaagatc tgcacactgg tatttcggtt tttggggccg      600
cgggcggcga cggggcccgt gcgtcccagc gcacatgttc ggcgaggcgg ggcctgcgag      660
cgcggccacc gagaatcgga cggggtagt ctcaagctgg ccggcctgct ctggtgcctg      720
gcctcgcgcc gccgtgtatc gccccgccct gggcggcaag gctggcccgg tcggcaccag      780
ttgcgtgagc ggaaagatgg ccgcttcccg gccctgctgc aggagctca aaatggagga      840 cgcggcgctc gggagagcgg gcgggtgagt cacccacaca aaggaaaagg gcctttccgt      900
cctcagccgt cgcttcatgt gactccactg agtaccgggc gccgtccagg cacctcgatt      960
agttctcgag cttttggagt acgtcgtctt taggttgggg gaggggtttt tatgcgatgg     1020
agtttcccca cactgagtgg gtggagactg aagttaggcc agcttggcac ttgatgtaat     1080
```

-continued

```
tctccttgga atttgccctt tttgagtttg gatcttggtt cattctcaag cctcagacag     1140
tggttcaaag ttttttctt ccatttcagg tgtcgtga                             1178

<210> SEQ ID NO 21
<211> LENGTH: 63
<212> TYPE: DNA
<213> ORGANISM: Artificial
<220> FEATURE:
<223> OTHER INFORMATION: signal peptide

<400> SEQUENCE: 21
atggccttac cagtgaccgc cttgctcctg ccgctggcct tgctgctcca cgccgccagg      60
ccg                                                                  63

<210> SEQ ID NO 22
<211> LENGTH: 135
<212> TYPE: DNA
<213> ORGANISM: Artificial
<220> FEATURE:
<223> OTHER INFORMATION: CD8 Hinge

<400> SEQUENCE: 22
accacgacgc cagcgccgcg accaccaaca ccggcgccca ccatcgcgtc gcagcccctg      60
tccctgcgcc cagaggcgtg ccggccagcg gcggggggcg cagtgcacac gaggggggctg     120 gacttcgcct gtgat                                                     135

<210> SEQ ID NO 23
<211> LENGTH: 72
<212> TYPE: DNA
<213> ORGANISM: Artificial
<220> FEATURE:
<223> OTHER INFORMATION: transmembrane domain

<400> SEQUENCE: 23
atctacatct gggcgccctt ggccgggact tgtggggtcc ttctcctgtc actggttatc      60
accctttact gc                                                        72

<210> SEQ ID NO 24
<211> LENGTH: 126
<212> TYPE: DNA
<213> ORGANISM: Artificial
<220> FEATURE:
<223> OTHER INFORMATION: 4-1BB

<400> SEQUENCE: 24
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                               126

<210> SEQ ID NO 25
<211> LENGTH: 336
<212> TYPE: DNA
<213> ORGANISM: Artificial
<220> FEATURE:
<223> OTHER INFORMATION: CD3_zeta

<400> SEQUENCE: 25
agagtgaagt tcagcaggag cgcagacgcc cccgcgtaca gcagggccga gaaccagctc      60
tataacgagc tcaatctagg acgaagagag gagtacgatg ttttggacaa gagacgtggc     120
```

-continued

```
cgggaccctg agatgggggg aaagccgaga aggaagaacc ctcaggaagg cctgtacaat        180
gaactgcaga aagataagat ggcggaggcc tacagtgaga ttgggatgaa aggcgagcgc        240
cggaggggca aggggcacga tggcctttac cagggtctca gtacagccac caaggacacc        300
tacgacgccc ttcacatgca ggccctgccc cctcgc                                 336
```

```
<210> SEQ ID NO 26
<211> LENGTH: 591
<212> TYPE: DNA
<213> ORGANISM: Artificial
<220> FEATURE:
<223> OTHER INFORMATION: WPRE

<400> SEQUENCE: 26
```

```
atcaacctct ggattacaaa atttgtgaaa gattgactgg tattcttaac tatgttgctc         60
cttttacgct atgtggatac gctgctttaa tgcctttgta tcatgctatt gcttcccgta        120
tggctttcat tttctcctcc ttgtataaat cctggttgct gtctctttat gaggagttgt        180
ggcccgttgt caggcaacgt ggcgtggtgt gcactgtgtt tgctgacgca accccccactg       240 gttggggcat tgccaccacc tgtcagctcc tttccgggac tttcgctttc ccctccccta        300
ttgccacggc ggaactcatc gccgcctgcc ttgcccgctg ctggacaggg gctcggctgt        360
tgggcactga caattccgtg gtgttgtcgg ggaagctgac gtcctttcca tggctgctcg        420
cctgtgttgc cacctggatt ctgcgcggga cgtccttctg ctacgtccct tcggccctca        480
atccagcgga ccttccttcc gcgggcctgc tgccggctct gcggcctctt ccgcgtcttc        540
gccttcgccc tcagacgagt cggatctccc tttgggccgc ctccccgcct g                 591
```

```
<210> SEQ ID NO 27
<211> LENGTH: 21
<212> TYPE: PRT
<213> ORGANISM: Artificial
<220> FEATURE:
<223> OTHER INFORMATION: signal peptide

<400> SEQUENCE: 27
```

```
Met Ala Leu Pro Val Thr Ala Leu Leu Leu Pro Leu Ala Leu Leu Leu
1               5                   10                  15

His Ala Ala Arg Pro
            20
```

```
<210> SEQ ID NO 28
<211> LENGTH: 45
<212> TYPE: PRT
<213> ORGANISM: Artificial
<220> FEATURE:
<223> OTHER INFORMATION: CD8 Hinge

<400> SEQUENCE: 28
```

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45
```

```
<210> SEQ ID NO 29
<211> LENGTH: 24
<212> TYPE: PRT
<213> ORGANISM: Artificial
<220> FEATURE:
```

<223> OTHER INFORMATION: transmembrane domain

<400> SEQUENCE: 29

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 30
<211> LENGTH: 42
<212> TYPE: PRT
<213> ORGANISM: Artificial
<220> FEATURE:
<223> OTHER INFORMATION: 4-1BB

<400> SEQUENCE: 30

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 31
<211> LENGTH: 112
<212> TYPE: PRT
<213> ORGANISM: Artificial
<220> FEATURE:
<223> OTHER INFORMATION: CD3_zeta

<400> SEQUENCE: 31

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
            85                  90                  95

Thr Lys Asp Thr Tyr Asp Ala Leu His Met Gln Ala Leu Pro Pro Arg
            100                 105                 110

<210> SEQ ID NO 32
<211> LENGTH: 2594
<212> TYPE: DNA
<213> ORGANISM: Artificial
<220> FEATURE:
<223> OTHER INFORMATION: CAR for lentivirus insertion

<400> SEQUENCE: 32
gctccggtgc ccgtcagtgg gcagagcgca catcgcccac agtccccgag aagttggggg      60
gaggggtcgg caattgaacc ggtgcctaga gaaggtggcg cggggtaaac tgggaaagtg     120
atgtcgtgta ctggctccgc ctttttcccg agggtggggg agaaccgtat ataagtgcag     180
tagtcgccgt gaacgttctt tttcgcaacg ggtttgccgc cagaacacag gtaagtgccg     240
tgtgtggttc ccgcgggcct ggcctcttta cgggttatgg cccttgcgtg ccttgaatta     300

```
cttccacctg gctgcagtac gtgattcttg atcccgagct tcgggttgga agtgggtggg      360
agagttcgag gccttgcgct taaggagccc cttcgcctcg tgcttgagtt gaggcctggc      420
ctgggcgctg gggccgccgc gtgcgaatct ggtggcacct tcgcgcctgt ctcgctgctt      480
tcgataagtc tctagccatt taaaattttt gatgacctgc tgcgacgctt tttttctggc      540
aagatagtct tgtaaatgcg ggccaagatc tgcacactgg tatttcggtt tttggggccg      600
cgggcggcga cggggcccgt gcgtcccagc gcacatgttc ggcgaggcgg ggcctgcgag      660
cgcggccacc gagaatcgga cgggggtagt ctcaagctgg ccggcctgct ctggtgcctg      720
gcctcgcgcc gccgtgtatc gccccgccct gggcggcaag gctggcccgg tcggcaccag      780
ttgcgtgagc ggaaagatgg ccgcttcccg gccctgctgc agggagctca aaatggagga      840
cgcggcgctc gggagagcgg gcgggtgagt cacccacaca aaggaaaagg gcctttccgt      900
cctcagccgt cgcttcatgt gactccactg agtaccgggc gccgtccagg cacctcgatt      960
agttctcgag cttttggagt acgtcgtctt taggttgggg ggaggggttt tatgcgatgg     1020
agtttcccca cactgagtgg gtggagactg aagttaggcc agcttggcac ttgatgtaat     1080
tctccttgga atttgccctt tttgagtttg gatcttggtt cattctcaag cctcagacag     1140
tggttcaaag ttttttttctt ccatttcagg tgtcgtgatc tagaggatcc gacatcgtga     1200
tgacccagag ccctttgtct cttcctgtca ctccgggggga gccagcttct atctcatgcc     1260
gatcttccaa gagcctgctg cactcaaatg gcatcaccta cctctattgg tacctgcaga     1320
agcccgggca atcccctcag ttgctcatct atcagatgtc taaccgcgcc tccggtgtcc     1380
ccgaccgctt cagctcctct ggctccggca ccgactttac tctgaagata tcccgcgtgg     1440
aggccgaaga tgtgggcgtg tactactgca ctcagaacct ggaactgccc ttcaccttcg     1500
gccagggcac caagctggag atcaagggcg gtggtggctc cggcggaggg ggttctggag     1560
gcggcggctc ccaggtgcag ctggtgcaga gcggcgccga ggtgaagaag ccgggtgctt     1620
ccgtgaaggt gtcctgtaag gcctctggct acaccttcac cagctacgtg atgcattggg     1680
tccgccaggc ccccggacag cgcctggagt ggatcggtta catcatcccg tacaacgacg     1740
gcactaagta caacgagaaa tttcagggcc gagtgaccct gacctccgac aaatccagct     1800
cgaccgccta catggagctg tcttctctgc gctcggagga caccgcggtt tattactgtg     1860
ctcgttggaa ctgggatggc tatttcgacg tgtggggcca gggaacgacc gtcaccgtgt     1920
cgtccaccac gacgccagcg ccgcgaccac caacaccggc gcccaccatc gcgtcgcagc     1980
ccctgtccct gcgcccagag gcgtgccggc cagcggcggg gggcgcagtg cacacgaggg     2040
ggctggactt cgcctgtgat atctacatct gggcgccctt ggccgggact tgtggggtcc     2100
ttctcctgtc actggttatc acccttttact gcaaacgggg cagaaagaaa ctcctgtata     2160
tattcaaaca accatttatg agaccagtac aaactactca agaggaagat ggctgtagct     2220
gccgatttcc agaagaagaa gaaggaggat gtgaactgag agtgaagttc agcaggagcg     2280
cagacgcccc cgcgtacaag cagggccaga accagctcta taacgagctc aatctaggac     2340
gaagagagga gtacgatgtt ttggacaaga cgtggccgg ggaccctgag atggggggaa      2400
agccgagaag gaagaaccct caggaaggcc tgtacaatga actgcagaaa gataagatgg     2460
cggaggccta cagtgagatt gggatgaaag cgagcgccg gaggggcaag gggcacgatg      2520
gcctttacca gggtctcagt acagccacca aggacaccta cgacgccctt cacatgcagg     2580 ccctgcccc tcgc                                                        2594
```

CHIMERIC ANTIGEN RECEPTOR TARGETING BCMA AND USE THEREOF

CROSS REFERENCE TO RELATED APPLICATIONS

This application is a National Stage entry under 35 U.S.C. § 371 of PCT/KR2021/006671, filed on May 28, 2021, and claims priority to Korean Patent Application No. 10-2020-0073714, filed on Jun. 17, 2020. The entire contents of both are incorporated herein by reference.

TECHNICAL FIELD

The present invention relates to a chimeric antigen receptor targeting BCMA and uses thereof, and more particularly, to an antibody targeting BCMA, a chimeric antigen receptor comprising the antibody, and a CAR-T cell expressing the chimeric antigen receptor.

BACKGROUND ART

Chimeric antigen receptor (CAR) T-cells are molecules that combine antibody-based specificity for a desired antigen with a T cell receptor-activating intracellular domain to generate chimeric proteins that exhibit specific anti-cancer immune activity. In general, a chimeric antigen receptor (CAR) comprises an extracellular antigen binding domain, a transmembrane domain and an intracellular signaling domain. The extracellular antigen binding domain can comprise a single-chain variable fragment (scFv) targeting the identified tumor antigen.

CARs can be expressed on the surface of T cells, which are immune effector cells, using genetic transfection techniques. Upon binding of a CAR expressed on the surface of a T cell to a target tumor antigen, the CAR can activate the T cell to initiate a specific antitumor response in an antigen-dependent manner.

Meanwhile, B-cell maturation antigen (BCMA), also known as CD269 or TNFRSF17, is a member of the tumor necrosis factor receptor family. It has been reported that BCMA can bind to B-cell activating factor receptor (BAFF) and B-cell proliferation-inducing ligand (APRIL) to promote survival of B cells at different developmental stages. Abnormal signaling can lead to abnormal proliferation of B cells, leading to autoimmune diseases such as multiple myeloma and tumorigenesis (Rickert, et al., Immunological Reviews, 2011, Vol. 244:115-133).

Multiple myeloma is a type of blood cancer that occurs when plasma cells are abnormally differentiated and proliferated, which creates tumors and melts bones, causing pain. In addition, multiple myeloma invades the bone marrow and decreases white blood cell, red blood cell, and platelet counts, increasing the risk of anemia, infection, and bleeding. Furthermore, myeloma cells also produce M protein, which is an abnormal immune protein, which increases the concentration of blood, causing blood hyperviscosity syndrome or damage to the kidneys.

Some treatments for multiple myeloma are similar to treatments for other cancers, such as chemotherapy or radiation therapy, stem cell transplantation or bone marrow transplantation, targeted therapy or biological therapy. Antibody-based cell immunotherapy has shown practical clinical benefit for patients with hematologic malignancies, particularly B-cell non-Hodgkin's lymphoma, but most patients have problems with relapse or secondary resistance, so an effective immunotherapeutic agent for treating multiple myeloma is required. For this purpose, a treatment method using CAR-T cells is being studied (Ellebrecht et al., Science 353:179-184, 2016; Carpenter et al., Clin Cancer Res, 19(8):2048-2060, 2013; WO2016-014789; WO 2016/014565; WO 2013/154760).

DISCLOSURE

Technical Problem

In the present invention, as a result of earnest efforts to develop a therapeutic agent for diseases related to B cells such as multiple myeloma, an antibody targeting BCMA was selected, and the selected anti-BCMA antibody was humanized to finally obtain a BCMA-targeting chimeric antigen receptor and a CAR-T cell were prepared. It was confirmed that the present BCMA-targeting CAR-T cell bound to BCMA and effectively killed BCMA-expressing tumor cells.

Accordingly, it is one of the objects of the present invention to provide an antibody targeting BCMA and a chimeric antigen receptor comprising the antibody.

Another object of the present invention is to provide a polynucleotide encoding a chimeric antigen receptor targeting BCMA, a vector comprising the same, and immune effector cells expressing the chimeric antigen receptor comprising the polynucleotide or the vector.

Another object of the present invention is to provide a pharmaceutical composition for preventing or treating a disease related to BCMA expression, including immune effector cells expressing the BCMA-targeting chimeric antigen receptor.

Technical Solution

In order to achieve the above object, the present invention can provide an antibody specifically binding to BCMA (B-cell maturation antigen) or fragment thereof, comprising: a heavy chain variable region including a CDR1 region represented by the amino acid sequence of SEQ ID NO: 1, a CDR2 region represented by the amino acid sequence of SEQ ID NO: 2, and a CDR3 region represented by the amino acid sequence of SEQ ID NO: 3; and a light chain variable region including a CDR1 region represented by the amino acid sequence of SEQ ID NO: 4, a CDR2 region represented by the amino acid sequence of SEQ ID NO: 5, and a CDR3 region represented by the amino acid sequence of SEQ ID NO: 6.

In a preferred embodiment of the present invention, the antibody can comprise a heavy chain variable region represented by the amino acid sequence of SEQ ID NO: 7 and a light chain variable region represented by the amino acid sequence of SEQ ID NO: 8; or a heavy chain variable region represented by the amino acid sequence of SEQ ID NO: 13 and a light chain variable region represented by the amino acid sequence of SEQ ID NO: 14.

In addition, the present invention can provide a chimeric antigen receptor (CAR) comprising: a BCMA-binding domain; a transmembrane domain; a costimulatory domain; and an intracellular signal transduction domain, wherein the BCMA-binding domain has an antibody specifically binding to BCMA or fragment thereof comprising: a heavy chain variable region comprising a CDR1 region represented by the amino acid sequence of SEQ ID NO: 1, a CDR2 region represented by the amino acid sequence of SEQ ID NO: 2 and a CDR3 region represented by the amino acid sequence of SEQ ID NO: 3; and a light chain variable region comprising a CDR1 region represented by the amino acid sequence of SEQ ID NO: 4, a CDR2 region represented by the amino acid sequence of SEQ ID NO: 5, and a CDR3 region represented by the amino acid sequence of SEQ ID NO: 6.

In a preferred embodiment of the present invention, the transmembrane domain may be derived from a protein selected from the group consisting of CD8a, CD4, CD28, CD137, CD80, CD86, CD152 and PD1.

In another preferred embodiment of the present invention, the costimulatory domain may be derived from a protein selected from the group consisting of CD28, 4-1BB, OX-40 and ICOS, and the signaling domain may be derived from CD3ζ.

In another preferred embodiment of the present invention, it may further include a hinge region located between the C-terminus of the BCMA-binding domain and the N-terminus of the transmembrane domain, wherein the hinge region is CD8a may be of origin.

To achieve another object, the present invention provides a polynucleotide encoding the chimeric antigen receptor (CAR).

The present invention also provides a vector comprising a polynucleotide encoding a chimeric antigen receptor (CAR).

In a preferred embodiment of the present invention, the vector may be a plasmid, a retroviral vector or a lentiviral vector.

In addition, the present invention provides an immune effector cell comprising a polynucleotide encoding the chimeric antigen receptor (CAR) or the vector comprising the polynucleotide encoding the chimeric antigen receptor (CAR).

In a preferred embodiment of the present invention, the immune effector cells may be T cells.

In order to achieve another object, the present invention provides a pharmaceutical for preventing or treating a disease relating to BCMA expression comprising an immune effector cell expressing the chimeric antigen receptor targeting BCMA or an antibody or fragment thereof that specifically binds to BCMA.

In a preferred embodiment of the present invention, the disease relating to BCMA expression may be multiple myeloma, hematologic cancer, non-Hodgkin's lymphoma, autoantibody-dependent autoimmune disease, systemic lupus erythematosus (SLE) or rheumatoid arthritis.

Advantageous Effects

It was confirmed that the chimeric antigen receptor and CAR-T cells targeting BCMA prepared in the present invention specifically bound to the antigen, BCMA, and activation of the BCMA-bound CAR-T cells was made.

In addition, since it was confirmed that the CAR-T cells of the present invention effectively killed BCMA-expressing cells, the chimeric antigen receptor and CAR-T cells targeting BCMA of the present invention can be usefully used for preventing or treating diseases related to B cell expression or BCMA expression.

MODE OF THE INVENTION

Figure 1:
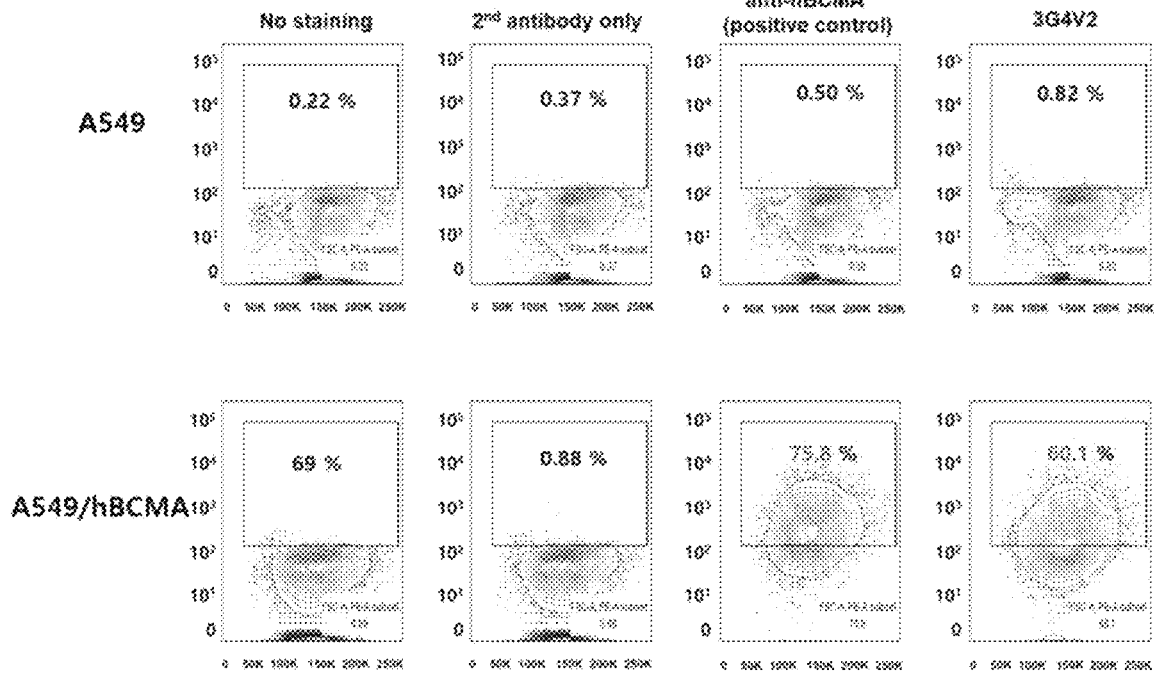
FIG. 1 is data confirming the BCMA binding ability of a humanized anti-BCMA monoclonal antibody (3G4V2).

Hereinafter, the present invention will be described in detail.

Antibodies Targeting BCMA

In one aspect, the present invention relates to an antibody specifically binding to BCMA (B-cell maturation antigen) or fragment thereof comprising: a heavy chain variable region including a CDR1 region represented by the amino acid sequence of SEQ ID NO: 1, a CDR2 region represented by the amino acid sequence of SEQ ID NO: 2, and a CDR3 region represented by the amino acid sequence of SEQ ID NO: 3; and a light chain variable region including a CDR1 region represented by the amino acid sequence of SEQ ID NO: 4, a CDR2 region represented by the amino acid sequence of SEQ ID NO: 5, and a CDR3 region represented by the amino acid sequence of SEQ ID NO: 6.

In the present invention, the antibody may be a monoclonal antibody. In the present invention, the term "monoclonal antibody" is an antibody produced by a single antibody-forming cell, and has a uniform primary structure (amino acid sequence). It recognizes only one antigenic determinant and is generally produced by culturing a hybridoma cell in which cancer cells and antibody-producing cells are fused. It can also be produced by using other recombinant protein expression host cells using the obtained antibody gene sequence.

In the present invention, the term "antibody" can be used not only in a complete form having two full-length light chains and two full-length heavy chains, but also as a fragment of an antibody molecule. A fragment of an antibody molecule refers to a fragment having at least a peptide tag (epitope) binding function, and includes scFv, Fab, F(ab'), F(ab')2, a single domain, and the like.

Among the antibody fragments, Fab has a structure having variable regions of light and heavy chains, a constant region of a light chain and a first constant region (CH1) of a heavy chain, and has one antigen-binding site. Fab' differs from Fab in that it has a hinge region comprising one or more cysteine residues at the C terminus of the heavy chain CH1 domain. The F(ab')2 antibody is produced by forming a disulfide bond with a cysteine residue in the hinge region of Fab'. Fv is a minimal antibody fragment having only a heavy chain variable region and a light chain variable region. Recombinant technology for generating Fv fragments is described in International Patent Publication Nos. WO 88/10649, WO 88/106630, WO 88/07085, WO 88/07086 and WO 88/09344. Double-chain Fv (dsFv) has a heavy chain variable region and a light chain variable region connected by a disulfide bond, and in single-chain Fv (scFv), the variable region of the heavy chain and the variable region of the light chain are generally covalently linked through a peptide linker. Such antibody fragments can be obtained using proteolytic enzymes (e.g., papain-restricted digestion of the entire antibody yields Fab, and pepsin digestion yields F(ab')₂ fragments). Preferably, it can be produced through genetic recombination technology.

In the present invention, the present monoclonal antibody specifically binding to BCMA can be prepared by using all or part of BCMA protein/peptide as an immunogen (or antigen). More specifically, first, as an immunogen, BCMA, a fusion protein comprising the BCMA protein, or a carrier comprising the BCMA protein, if necessary, together with an adjuvant (e.g., Freund adjuvant), is injected once or more by subcutaneous, intramuscular, intravenous, intraperitoneal in mammals except for humans to achieve an immunization. The mammals other than humans are preferably mice, rats, hamsters, malmots, chickens, rabbits, cats, dogs, pigs, goats, sheep, donkeys, horses or cattle (including transgenic animals engineered to produce an antibody from other animals such as mice to produce human antibody), more preferably mouse, rat, hamster, malmot, chicken or rabbit. Antibody-producing cells can be obtained from the immune-sensitized mammal about 1 to 10 days after the final immunization by performing immunization 1 to 4 times every 1 to 21 days from the first immunization. The number of times and intervals for immunization can be appropriately changed depending on the characteristics of the immunogen to be used.

Preparation of a hybridoma secreting a monoclonal antibody can be carried out according to the method of Keira and Mirstein et al. (Nature, 1975, Vol. 256, p. 495-497) and a method similar thereto. Hybridomas can be produced by cell fusion of mammal-derived myeloma cells without autologous antibody-producing ability and antibody-producing cells contained in the group consisting of spleen, lymph node, bone marrow and tonsils, preferably spleen.

For cell fusion, for example, a fusion promoter including polyethylene glycol or Sendai virus or a method by electric pulse is used, for example, antibody-producing cells and mammalian-derived cells capable of indefinite proliferation are suspended at a ratio of about 1:1 to 1:10 in a fusion medium containing a fusion promoter, and in this state, cultured at about 30 to 40° C. for about 1 to 5 minutes. As the fusion medium, for example, MEM medium, RPMI1640 medium, and Iscove's Modified Dulbecco's Medium may be used, and it is preferable to exclude serums such as bovine serum.

In the method of screening the hybridoma clones producing the monoclonal antibody, first, the fusion cells obtained as described above are transferred to a selection medium such as HAT medium, and cultured at about 30 to 40° C. for about 3 days to 3 weeks to kill cells other than hybridomas. Then, after culturing the hybridoma on a microtiter plate, etc., the part with increased reactivity between the immunogen used for the immune response of animals other than humans described above and the culture supernatant was subjected to RIA (radioactive substance-marked immuno antibody) or ELISA (Enzyme-Linked Immunosorbent Assay). The clone producing the monoclonal antibody found above shows specific binding ability to the immunogen.

The monoclonal antibody of the present invention can be obtained by culturing such a hybridoma in vitro or in vivo. For culturing, a conventional method for culturing cells derived from mammals is used, and for collecting monoclonal antibody from a culture or the like, a conventional method in this field for purifying an antibody in general is used. As each method, for example, salting out, dialysis, filtration, concentration, centrifugation, fractional precipitation, gel filtration chromatography, ion exchange chromatography, affinity chromatography, high-performance liquid chromatography, gel electrophoresis or isoelectric point electrophoresis, etc. can be applied, and these are applied in combination as needed. The purified monoclonal antibody is then concentrated and dried to be in a liquid or solid state depending on the use.

In addition, the monoclonal antibody of the present invention can be obtained by: synthesized each ligated gene of DNAs encoding heavy chain and light chain variable regions, respectively, with known DNA encoding the constant regions of heavy chain and light chain (e.g., Japan patent publication No. 2007-252372) by PCR or chemical synthesis; transplanted into a known expression vector that enables expression of the gene, etc. to prepare a transformant; producing an antibody by expressing it in a host of CHO cells, *Escherichia coli*, etc.; and purifying the antibody from this culture solution using a protein A or G column or the like.

In a specific embodiment of the present invention, a mouse antibody that specifically binds to BCMA was prepared and screened to establish a novel antibody, which was named 3G4.

In the present invention, it was confirmed that the present 3G4 antibody comprised a heavy chain variable region having a CDR1 region represented by the amino acid sequence of SEQ ID NO: 1 (GYTFTSYV), a CDR2 region represented by the amino acid sequence of SEQ ID NO: 2 (IIPYNDGT), and a CDR3 region represented by the amino acid sequence of SEQ ID NO: 3 (ARWNWDGYFDV); and a light chain variable having a CDR1 region represented by the amino acid sequence of SEQ ID NO: 4 (KSLLHSN-GITY), a CDR2 region represented by the amino acid sequence of SEQ ID NO: 5 (QMS), and a CDR3 region represented by the amino acid sequence of SEQ ID NO: 6 (TQNLELPFT).

Preferably, the 3G4 antibody can be composed of a heavy chain variable region represented by the amino acid sequence of SEQ ID NO: 7 and a light chain variable region represented by the amino acid sequence of SEQ ID NO: 8. In addition, the heavy chain variable region of the 3G4 antibody may be encoded by the nucleotide sequence of SEQ ID NO: 9, and the light chain variable region of the 3G4 antibody may be encoded by the nucleotide sequence of SEQ ID NO: 10. When the 3G4 antibody exists in scFv form, it may be linked to a light chain variable region-linker-heavy chain variable region, and preferably encoded by the amino acid sequence of SEQ ID NO: 11 or the nucleotide sequence of SEQ ID NO: 12.

In another specific embodiment of the present invention, a humanized antibody obtained by changing the anti-BCMA antibody 3G4 into a structure corresponding to a human was prepared, which was named 3G4V2.

The heavy chain variable region CDRs and light chain variable region CDRs of 3G4V2 are the same as those of 3G4, and the remaining parts except for the CDR part were humanized. Preferably, 3G4V2 can be composed of a heavy chain variable region represented by the amino acid sequence of SEQ ID NO: 13 and a light chain variable region represented by the amino acid sequence of SEQ ID NO: 14. In addition, the heavy chain variable region of the 3G4V2 antibody may be encoded by the nucleotide sequence of SEQ ID NO: 15, and the light chain variable region of the 3G4V2 antibody may be encoded by the nucleotide sequence of SEQ ID NO: 16. When the 3G4 antibody exists in scFv form, it may be linked to a light chain variable region-linker-heavy chain variable region, and preferably encoded by the amino acid sequence of SEQ ID NO: 17 or the nucleotide sequence of SEQ ID NO: 18.

In another specific embodiment of the present invention, as a result of confirming whether the humanized anti-BCMA antibody 3G4V2 and BCMA specifically bind, as shown in FIG. 1, binding to 3G4V2 was not confirmed in A549 cells in which hBCMA is not expressed. However, it was confirmed that the binding capacity of A549 cells expressing hBCMA and 3G4V2 was increased.

Therefore, in the present invention, a chimeric antigen receptor (CAR) targeting BCMA was prepared using a humanized anti-BCMA antibody, 3G4V2.

As used herein, the term "humanized antibody" is an antibody that possesses an amino acid sequence corresponding to that of an antibody produced by a human and/or is made using one of the techniques for making human antibodies as disclosed herein. This definition of a humanized antibody specifically excludes a humanized antibody comprising non-human antigen-binding residues.

In addition, it should be understood that the protein, polypeptide and/or amino acid sequence encompassed by the present invention includes functional variants or homologues having at least the same or similar function as the protein or polypeptide.

In the present invention, functional variants may be a protein or polypeptide obtained by substituting, deleting or adding one or more amino acids in the amino acid sequence of the protein and/or polypeptide. Functional variants are capable of substantially retaining the biological properties of an unmodified protein or polypeptide. For example, functional variants may retain at least 60%, 70%, 80%, 90% or 100% of the biological activity (such as antigen binding capacity) of the original protein or polypeptide.

In the present invention, homologues may be a protein or polypeptide having at least about 85% (e.g., about 85%, 90%, 91%, 92%, 93%, 94%, 95%, 96%, 97%, 98%, 99% or more) amino acid sequence homology with the protein and/or polypeptide (e.g., an antibody capable of specifically binding BCMA or a fragment thereof).

In the present invention, homology generally refers to similarity, similarity or correlation between two or more sequences.

Chimeric Antigen Receptor Targeting BCMA

The present invention from another point of view, also relates to a chimeric antigen receptor (CAR) comprising: a BCMA-binding domain; a transmembrane domain; a costimulatory domain; and an intracellular signal transduction domain, wherein the BCMA-binding domain includes an antibody or fragment thereof capable of specifically binding BCMA comprising: a heavy chain variable region comprising a CDR1 region represented by the amino acid sequence of SEQ ID NO: 1, a CDR2 region represented by the amino acid sequence of SEQ ID NO: 2 and a CDR3 region represented by the amino acid sequence of SEQ ID NO: 3, and a light chain variable region comprising a CDR1 region represented by the amino acid sequence of SEQ ID NO: 4, a CDR2 region represented by the amino acid sequence of SEQ ID NO: 5, and a CDR3 region represented by the amino acid sequence of SEQ ID NO: 6.

As used herein, the term "chimeric antigen receptor (CAR)" generally refers to a fusion protein containing an extracellular domain having the ability to bind an antigen and one or more intracellular domains. A CAR is a core part of a chimeric antigen receptor T cell (CAR-T) and may contain an antigen binding domain, a transmembrane domain, a co-stimulatory domain, and an intracellular signal transduction domain. A CAR can be combined with a T cell receptor-activating intracellular domain based on the antigen (e.g., BCMA) specificity of the antibody. Genetically modified CAR-expressing T cells can specifically identify and eliminate target antigen-expressing malignant cells.

In the present invention, the term "BCMA" refers to a B-cell maturation antigen. BCMA (also known as TNFRSF17, BCM or CD269) is a member of the tumor necrosis receptor (TNFR) family and is predominantly expressed on terminally differentiated B cells, such as memory B cells and plasma cells. BCMA is expressed on tumor cells (e.g., multiple myeloma cells) or localized on the surface of tumor cells. "BCMA" of the present invention may include proteins comprising mutations of full-length wild-type BCMA, e.g., point mutations, fragments, insertions, deletions and splice variants.

In the present invention, the term "BCMA-binding domain" generally refers to a domain capable of specifically binding to a BCMA protein. For example, the BCMA-binding domain may contain an anti-BCMA antibody or fragment thereof capable of specifically binding to a human BCMA polypeptide or fragment thereof expressed in a B cell.

In the present invention, the term "binding domain" can be used interchangeably refers to "extracellular domain", "extracellular binding domain", "antigen-specific binding domain" and "extracellular antigen-specific bidding domain" and refers to a CAR domain or fragment having the ability to specifically bind a target antigen (e.g., BCMA).

In the present invention, the anti-BCMA antibody or fragment thereof is the above-described anti-BCMA antibody, a monoclonal antibody, preferably a single chain variable fragment (scFv), and in the present invention, a humanized anti-BCMA antibody, 3G4V2 was used.

In the present invention, the term "transmembrane domain" generally refers to a domain of a CAR that passes through a cell membrane and is connected to an intracellular signaling domain to play a signaling role. The transmembrane domain may be derived from a protein selected from the group consisting of CD8a, CD4, CD28, CD137, CD80, CD86, CD152 and PD1, and may preferably be represented by the amino acid sequence of SEQ ID NO: 29.

In the present invention, the term "costimulatory domain" generally refers to an intracellular domain capable of providing immune-stimulatory molecules, which are cell surface molecules required for an effective response of lymphocytes to antigens. The costimulatory domain described above may comprise a costimulatory domain of CD28, and may comprise a costimulatory domain of the TNF receptor family, such as the costimulatory domain of OX40 and 4-1BB, and preferably it may be 4-1BB represented by the amino acid sequence of SEQ ID NO: 30.

In the present invention, the term "intracellular signal transduction domain" generally refers to a domain located inside a cell and capable of transmitting a signal. In the present invention, the intracellular signaling domain is the intracellular signaling domain of the chimeric antigen receptor. For example, the intracellular signaling domain may be selected from CD3ζ intracellular domain, CD28 intracellular domain, CD28 intracellular domain, 4-1BB intracellular domain and OX40 intracellular domain, and preferably it may be CD3ζ represented by the amino acid sequence of SEQ ID NO: 31.

In the present invention, it may further comprise a hinge region located between the C terminus of the BCMA-binding domain and the N terminus of the transmembrane domain, wherein the hinge region is derived from CD8a, and preferably it can be represented by the amino acid sequence of SEQ ID NO: 28. The "hinge region" generally refers to a linking region between an antigen-binding region and an immune cell Fc receptor (FcR)-binding region.

In the present invention, it may further include a signal peptide at the N-terminus of the BCMA-binding domain, and the "signal peptide" generally refers to a peptide chain for guiding protein transduction. The signal peptide may be a short peptide having a length of 5 to 30 amino acids, preferably represented by the amino acid sequence of SEQ ID NO: 27.

Chimeric Antigen Receptor Encoding Polynucleotides and Chimeric Antigen Receptor Expression Vectors In another aspect, the present invention relates to a polynucleotide encoding the chimeric antigen receptor (CAR).

In the present invention, the polynucleotide encoding the chimeric antigen receptor (CAR) has a polynucleotide encoding a BCMA-binding domain; a polynucleotide encoding a transmembrane domain; polynucleotides encoding the co-stimulatory domain; and a polynucleotide encoding an intracellular signal transduction domain.

A polynucleotide encoding the BCMA-binding domain may preferably be a polynucleotide encoding a 3G4 antibody or a 3G4V2 antibody, and the specific nucleotide sequence is as described above.

A polynucleotide encoding the chimeric antigen receptor (CAR) of the present invention may has a signal peptide represented by the nucleotide sequence of SEQ ID NO: 21; 3G4V2, which is an anti-BCMA antibody represented by the nucleotide sequence of SEQ ID NO: 18; a transmembrane domain represented by the nucleotide sequence of SEQ ID NO: 23; 4-1BB (costimulatory domain) represented by the nucleotide sequence of SEQ ID NO: 24; and CD3ζ (intracellular signaling domain) represented by the nucleotide sequence of SEQ ID NO: 25.

In addition, a polynucleotide encoding a hinge region may be additionally included between a polynucleotide encoding the BCMA-binding domain and a transmembrane domain, and preferably It may be a CD8 hinge region represented by the nucleotide sequence of SEQ ID NO: 22.

As used herein, the term "polynucleotide" generally refers to a nucleic acid molecule, deoxyribonucleotide or ribonucleotide, or an analog thereof, separated by any length. In some embodiments, a polynucleotide of the present invention can be prepared by (1) in-vitro amplification, such as polymerase chain reaction (PCR) amplification; (2) cloning and recombination; (3) purification such as digestion and gel electrophoretic separation; (4) synthesis such as chemical synthesis, and preferably, the isolated polynucleotide is prepared by recombinant DNA technology. In the present invention, the nucleic acid for encoding the antibody or antigen-binding fragment thereof can be prepared by various methods known in the art, including, but not limited to, restriction fragment operation of synthetic oligonucleotides or application of SOE PCR.

In another aspect, the present invention relates to a vector comprising a polynucleotide encoding the chimeric antigen receptor (CAR).

In the present invention, the term "vector (expression vector)" refers to a gene preparation including essential regulatory elements such as a promoter so that a target gene can be expressed in an appropriate host cell. A vector may be selected from one or more of a plasmid, a retroviral vector, and a lentiviral vector. Upon transformation into an appropriate host, a vector can replicate and function independently of the host genome, or in some cases can be integrated into the genome itself.

In addition, a vector may contain expression control elements that allow the coding region to be accurately expressed in a suitable host. Such regulatory elements are well known to those skilled in the art and include, for example, promoters, ribosome-binding sites, enhancers and other regulatory elements for regulating gene transcription or mRNA translation. The specific structure of the expression control sequence may vary depending on the function of the species or cell type, but generally contains 5' non-translated sequence, and a 5' or 3' non-translated sequence participating in transcription initiation and translation initiation, respectively, such as TATA box, capped sequence, CAAT sequence, etc. For example, a 5' non-transcriptional expression control sequence can include a promoter region that can include a promoter sequence for transcription and control of a functionally linked nucleic acid.

Figure 2:
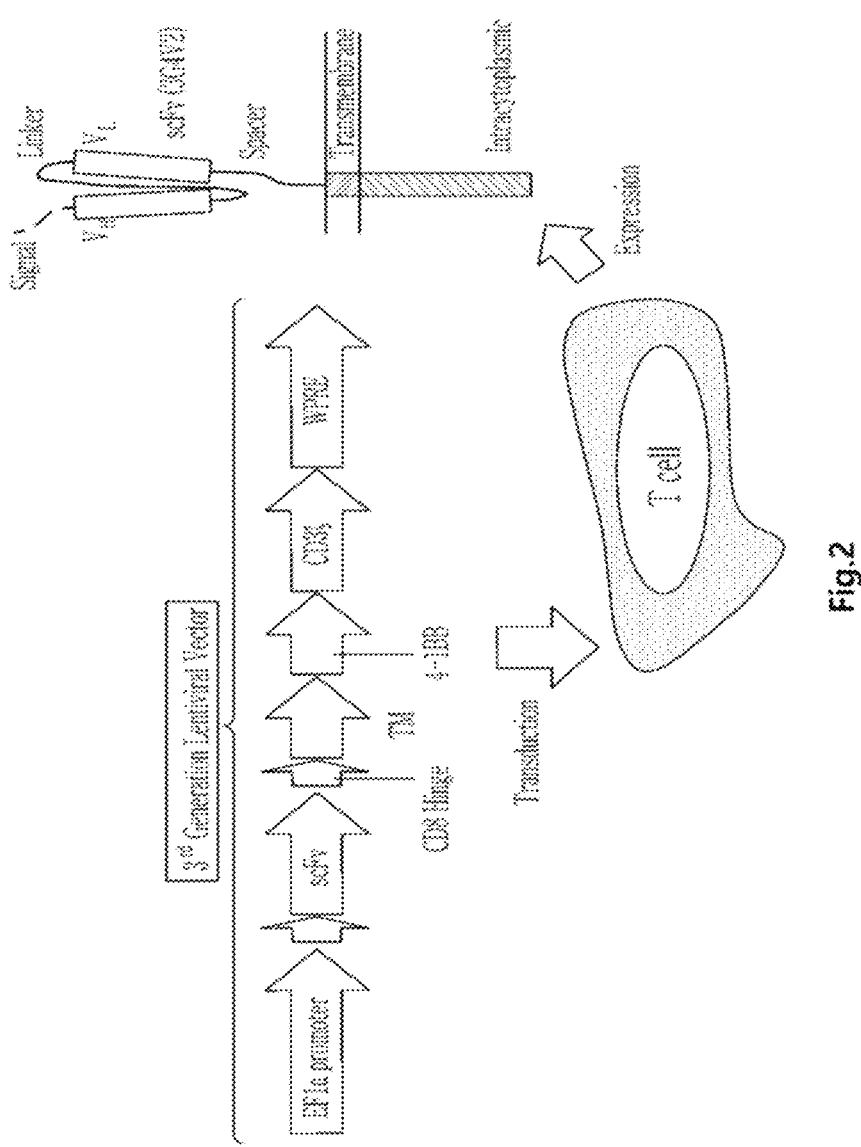
FIG. 2 is a schematic diagram illustrating the lentiviral vector expressing a chimeric antigen receptor (hBCMA-CAR) targeting BCMA and a chimeric antigen receptor expressed in T cells.

In a specific embodiment of the present invention, the vector is a recombinant virus a vector, preferably a lentivirus vector, and comprises an operably linked EF1α promoter; a polynucleotide encoding a signal peptide; a polynucleotide encoding a BCMA-binding domain; a polynucleotide encoding a transmembrane domain; and a polynucleotide encoding an intracellular signal transduction domain, and may further include a woodchuck hepatitis virus post-transcriptional regulatory element (WPRE) to increase protein expression (refer to FIG. 2).

The EF1α promoter may be represented by the nucleotide sequence of SEQ ID NO: 87, and if necessary, has 90% or more, 93% or more, 95% or more, 96% or more, 97% or more, 98% or more, or 99% or more identical sequences of the nucleotide sequence of SEQ ID NO: 19.

In addition, the promoter is operably linked to induce expression of an anti-hBCMA antibody (scFv), which is a BCMA-binding domain, wherein "operably linked" refers to a nucleic acid expression control sequence and a nucleic acid sequence encoding a target protein are functionally linked to perform a general function. The operative linkage with the recombinant vector can be prepared using genetic recombination techniques well known in the art, and site-specific DNA cleavage and ligation using enzymes generally known in the art.

Methods for introducing and expressing genes into cells are known in the art. With respect to expression vectors, vectors can be readily introduced into host cells by any method in the art. For example, an expression vector may be transferred into a host cell by physical, chemical, or biological means.

Physical methods for introducing polynucleotides into host cells include calcium phosphate precipitation, lipofection, particle bombardment, microinjection, electroporation, and the like. Methods for producing cells comprising vectors and/or exogenous nucleic acids are well known in the art. See, e.g., Sambrook et al, 2012, MOLECULAR CLONING: A LABORATORY MANUAL, volumes 1-4, Cold Spring Harbor Press, NY. A preferred method for introduction of polynucleotides into host cells is calcium phosphate transfection.

Biological methods for introducing polynucleotides into host cells include the use of DNA and RNA vectors. Viral vectors, and in particular retroviral vectors, have become the most widely used methods for inserting genes into mammalian, e.g., human cells. Other viral vectors may be derived from lentiviruses, poxviruses, herpes simplex viruses, adenoviruses and adeno-associated viruses, and the like.

Chemical means for introducing polynucleotides into host cells include colloidal dispersion systems such as macromolecular complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). State of the art in targeted delivery of nucleic acids, such as targeted other methods for delivery of polynucleotides using nanoparticles or other suitable sub-micron sized delivery systems are available.

When a non-viral delivery system is used, an exemplary delivery vehicle is a liposome. The use of lipid preparations is contemplated for the introduction of nucleic acids into host cells (in vitro, ex vivo or in vivo). In another aspect, the nucleic acid may be associated with a lipid. Nucleic acids associated with lipids may be encapsulated within the aqueous interior of the liposome, interspersed within the lipid bilayer of the liposome, attached to the liposome via a linking molecule associated with both the liposome and oligonucleotide, captured within the liposome, complexed with the liposome, dispersed in a lipid-containing solution, mixed with a lipid or combined with a lipid, contained as a suspension in a lipid, contained or complexed with micelles, or otherwise associated with a lipid. Lipid, lipid/DNA or lipid/expression a vector association composition is not limited to any particular structure in solution.

Immune Effector Cells Expressing Chimeric Antigen Receptor (CAR)

In another aspect, the present invention relates to an immune effector cell expressing the chimeric antigen receptor (CAR), and includes a vector comprising a polynucleotide encoding a chimeric antigen receptor (CAR), or a polynucleotide encoding a chimeric antigen receptor (CAR).

In the present invention, the immune effector cell may be a mammalian-derived cell, preferably a T cell or a natural killer (NK) cell.

In the present invention, an immune effector cell expressing the chimeric antigen receptor (CAR) can be prepared by introducing the CAR vector of the present invention into an immune effector cell, for example, a T cell or NK cell.

Specifically, CAR vector can be introduced into cells by methods known in the art, such as electroporation, lipofectamine (lipofectamine 2000, Invitrogen), and the like. For example, an immune effector cell can be transformed by a lentiviral vector to integrate the viral genome carrying the CAR molecule into the host genome to ensure long-term and stable expression of the target gene. For another example, a transposon can be used to introduce a CAR transport plasmid and a transferase transport plasmid into a target cell. For another example, a CAR molecule can be added to the genome by a gene editing method (e.g., CRISPR/Cas9).

In a specific embodiment of the present invention, as shown in FIG. 2, a lentiviral vector into which a polynucleotide coating hBCMA-CAR was inserted was prepared, and the prepared vector was transformed into T cells to prepare hBCMA-CAR-T cells. The prepared hBCMA-CAR-T cells can express a chimeric antigen receptor targeting BCMA of the present invention.

An immune effector cell for the production of immune effector cell expressing a chimeric antigen receptor (CAR) can be obtained from a subject, wherein the "subject" includes a living organism (e.g., a mammal from which an immune response can be elicited). Examples of subjects include humans, dogs, cats, mice, rats, and transgenic species thereof. T cells can be obtained from numerous sources, including peripheral blood mononuclear cells, bone marrow, lymph node tissue, umbilical cord blood, thymus tissue, tissue from the site of infection, ascites, pleural effusion, splenic tissue, and tumors.

Such T cells can be obtained from blood units collected from a subject using any of a number of techniques known to those of ordinary skill in the art, for example, Ficoll™ isolation. Cells from blood are obtained by apheresis, and apheresis products typically contain T cells, monocytes, granulocytes, lymphocytes including B cells, other nucleated leukocytes, red blood cells, and platelets.

Cells collected by apheresis can be washed to remove the plasma fraction and place the cells in an appropriate buffer or medium for subsequent processing steps. T cells are isolated from peripheral blood lymphocytes by lysing red blood cells and depleting monocytes, for example by centrifugation through a PERCOLL™ gradient or by countercurrent centrifugation.

Figure 3:
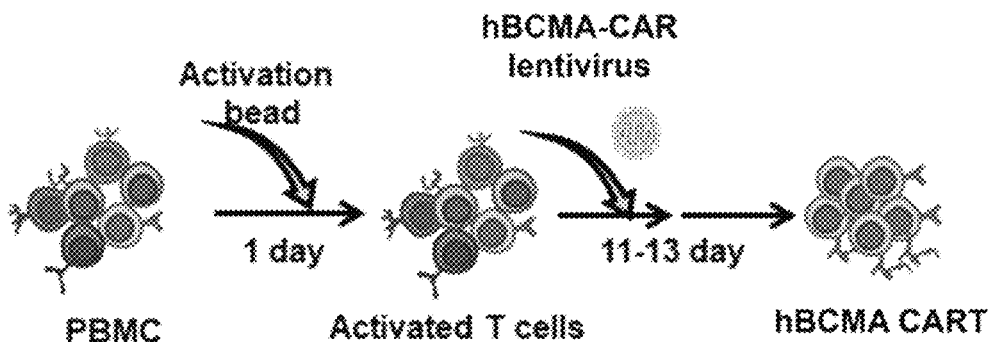
FIG. 3 is a schematic diagram illustrating a method for preparing hBCMA-CAR-T cells using the lentivirus expressing hBCMA-CAR.
Figure 4:
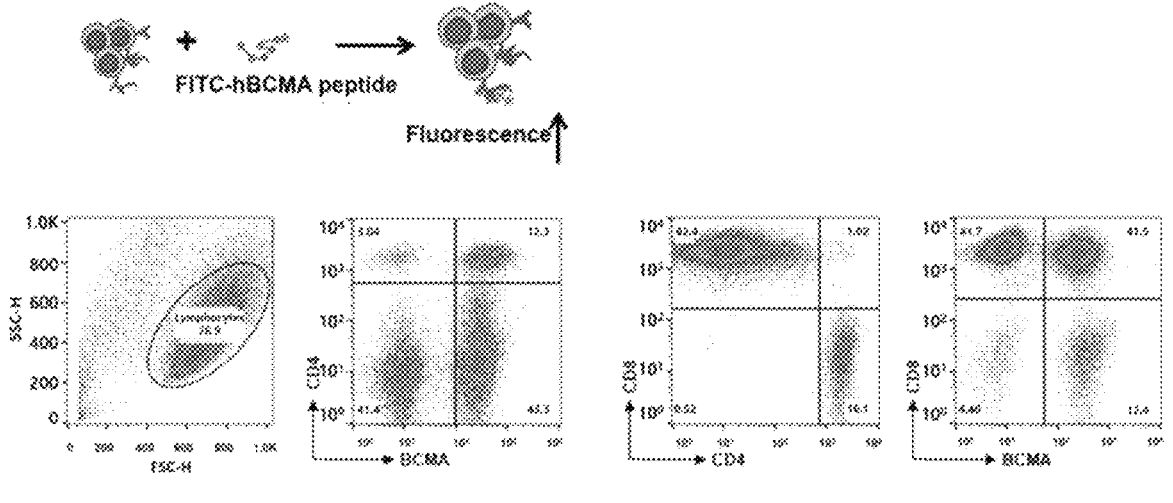
FIG. 4 is data confirming the BCMA binding ability of hBCMA-CAR-T cells.

In a specific embodiment of the present invention, as shown in FIG. 3, activated T cells were isolated from peripheral blood mononuclear cells (PBMCs), and then, hBCMA-CAR lentivirus was transduced into T cells, and hBCMA-CAR-T cells were prepared. As a result of confirming the hBCMA peptide binding ability of the prepared hBCMA-CAR-T cells, as shown in FIG. 4, as the hBCMA peptide increased, it was confirmed that the hBCMA-CAR-T cells expressing CD4 or CD8 binding to hBCMA increased. This means that the hBCMA-CAR-T cells prepared in the present invention effectively can bind BCMA.

Figure 5:
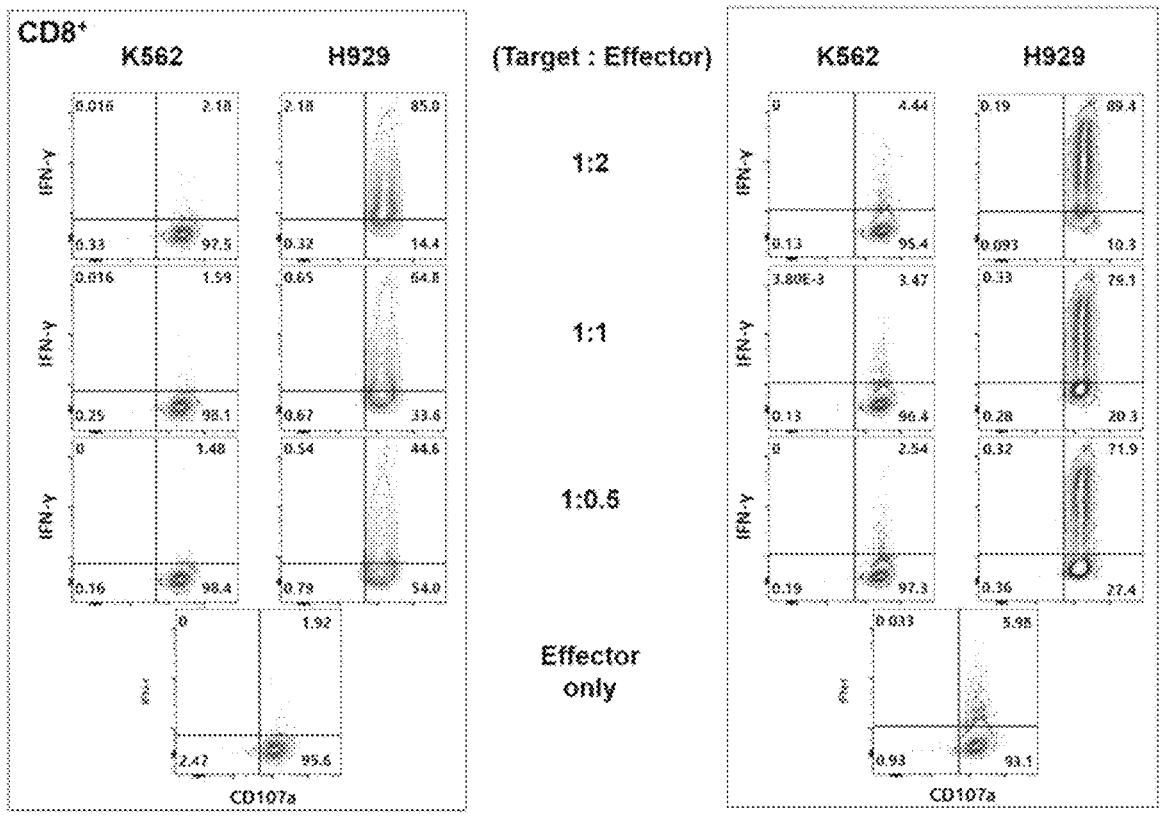
FIG. 5 is data confirming the expression level of IFNγ and CD107a by 3G4V2-CART cells in the presence of target cells in order to confirm the activation of hBCMA-CAR-T cells.

In a specific embodiment of the present invention, in order to confirm the activation of hBCMA-CAR-T cells, the expression level of IFNγ and CD107a by 3G4V2-CAR-T cells in the presence of target cells was checked. As a result, as shown in FIG. 5, T cells were not activated in BCMA-expressing K562 cells, whereas T cells were activated in the presence of BCMA-expressing H929 cells to increase IFNγ expression.

Figure 6:
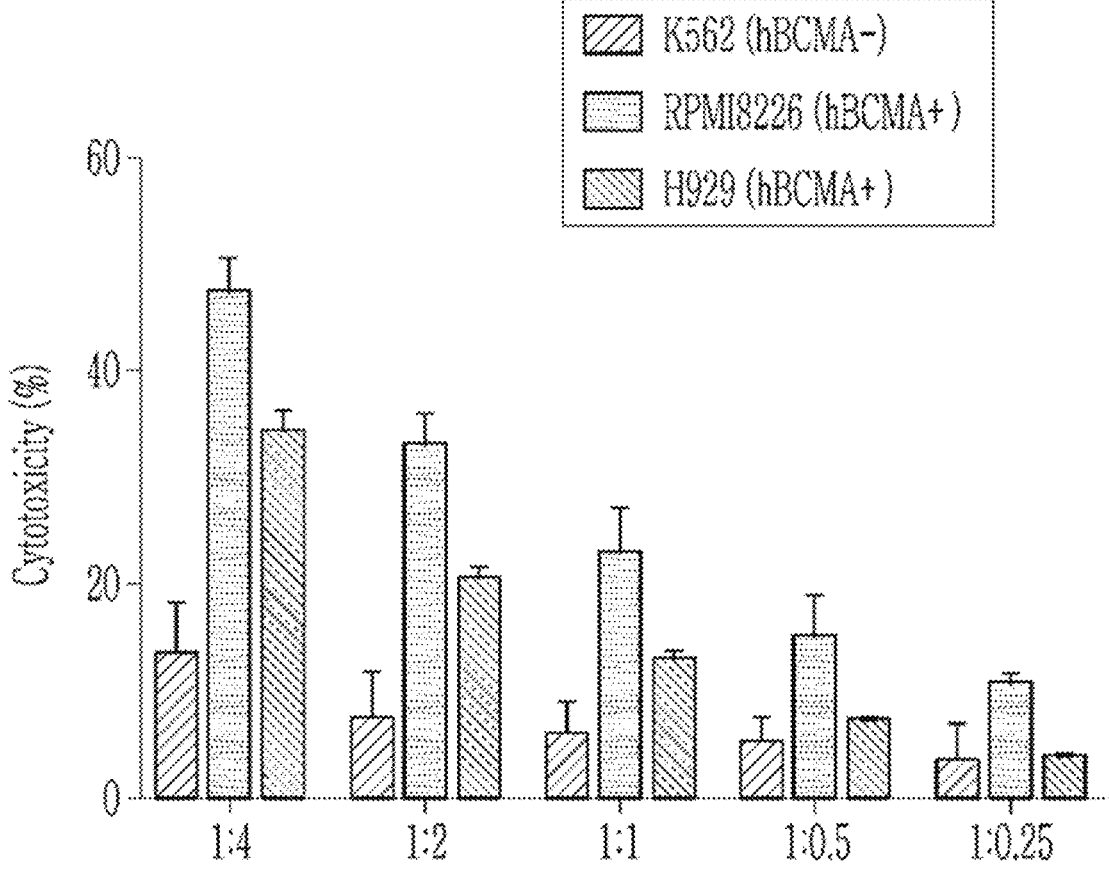
FIG. 6 is data confirming the killing effect of target cells by hBCMA-CAR-T cells.

In a specific embodiment of the present invention, as a result of confirming the killing effect of the target cells by the hBCMA-CAR-T cells, as shown in FIG. 6, it was confirmed that hBCMA-CAR-T cells specifically killed RPMI8226 cells and H929 cells expressing BCMA.

That is, the chimeric antigen receptor and CAR-T cell targeting BCMA of the present invention can be usefully used as a composition for preventing or treating diseases related to B cell expression or BCMA expression.

Composition for Preventing or Treating Diseases Related to BCMA Expression

In another aspect, the present invention relates to a pharmaceutical composition for preventing or treating diseases related to B cells, including immune effector cells expressing a chimeric antigen receptor targeting BCMA.

In another aspect, the present invention relates to a pharmaceutical composition for preventing or treating diseases related to B cells comprising an antibody targeting BCMA.

A disease associated with B cells or a disease associated with BCMA (wild-type or mutant BCMA) expression may be cancer, malignancy or an autoimmune disease. Preferably multiple myeloma, hematological cancer, non-Hodgkin It may be non-Hodgkin's lymphoma, autoantibody-dependent autoimmune disease, systemic lupus erythematosus (SLE) or rheumatoid arthritis.

The pharmaceutical composition may further include a pharmaceutically acceptable carrier. For oral administration, binders, lubricants, disintegrants, excipients, solubilizers, dispersants, stabilizers, suspending agents, pigments, fragrances, etc. can be used. In the case of an injection, a buffer, a preservative, an analgesic, a solubilizer, an isotonic agent, a stabilizer, and the like may be mixed and used. In the case of topical administration, bases, excipients, lubricants, preservatives, etc. can be used.

The formulation of the pharmaceutical composition may be prepared in various ways by mixing with the above-described pharmaceutically acceptable carrier. For example, in the case of oral administration, it may be prepared in the form of tablets, troches, capsules, elixirs, suspensions, syrups, wafers, and the like, and in the case of injections, it may be prepared in the form of unit dose ampoules or multiple doses.

In addition, the pharmaceutical composition may include a surfactant capable of improving membrane permeability. Such surfactants may be steroid-derived or cationic lipids such as N-[1-(2,3-dioleoyl)propyl-N,N,N-trimethylammonium chloride (DOTMA), or cholesterol hemisuccinate, various compounds such as phosphatidyl glycerol, but is not limited thereto.

In addition, the present invention provides a method for preventing or treating cancer, comprising administering the pharmaceutical composition according to the present invention to a subject. The pharmaceutical composition comprising the hBCMA-CAR-T cell or anti-hBCMA antibody may be administered in a pharmaceutically effective amount to prevent or treat a disease associated with B cells. It may vary depending on various factors such as the type of disease, the age and weight of the patient, the characteristics and severity of symptoms, the type of current treatment, the number of treatments, the dosage form, and route, and may be easily determined by experts in the field.

The pharmaceutical composition may be administered together or sequentially with the aforementioned pharmacological or physiological ingredient, and may be administered in combination with an additional conventional therapeutic agent, or may be administered sequentially or simultaneously with the conventional therapeutic agent. Such administration may be single or multiple administrations. Taking all of the above factors into consideration, it is important to administer an amount that can obtain the maximum effect with a minimum amount without side effects, which can be easily determined by those skilled in the art.

As used herein, the term "subject" refers to a mammal suffering from or at risk of a condition or disease that can be alleviated, suppressed or treated by administering the pharmaceutical composition, and preferably refers to a human.

As used herein, the term 'administration' refers to providing the pharmaceutical composition of the present invention to an individual by any suitable method. The pharmaceutical composition of the present invention provides an amount of an active ingredient or pharmaceutical composition that induces a biological or medical response in a tissue system, animal or human as thought by a researcher, veterinarian, doctor or other clinician, that is, alleviation of symptoms of a disease or disorder to be treated. It can be administered in a therapeutically effective amount, which is an amount that induces It is apparent to those skilled in the art that the therapeutically effective dosage and frequency of administration for the pharmaceutical composition of the present invention will vary depending on the desired effect. Therefore, the optimal dosage to be administered can be easily determined by those skilled in the art, and the type of disease, the severity of the disease, the content of active ingredients and other components contained in the composition, the type of formulation, the age, weight, and general health of the patient, gender and diet, administration time, administration route and secretion rate of the composition, treatment period, and various factors including concurrently used drugs. The pharmaceutical composition of the present invention may be administered in an amount of 1 to 10,000 mg/kg/day, may be administered once a day, or may be administered in divided doses.

Hereinafter, preferred examples are presented to help the understanding of the present invention. However, the following examples are only provided for easier understanding of the present invention, and the contents of the present invention are not limited by the following examples.

Example 1: Preparation and Selection of the Antibody Targeting BCMA

In order to select the BCMA peptide-specific antibody, a hybridoma producing an antibody binding to BCMA was prepared and the antibody was selected.

First, mice were immunized using a BCMA peptide (SEQ ID NO: 19; Acrobiosystems Inc. cat #BCA-H522γ) by a method known in the art, and then splenocytes were extracted and hybridomas cells were prepared through cell fusion with mouse myeloma cells.

Mouse myeloma cells used for cell fusion cannot survive in HAT medium because they do not have HGPRT (HypoxanthineGuanidine-Phosphoribosyl-Transferase), but hybridomas can survive in HAT medium by fusion with splenocytes. Since only hybridomas could be grown using this, it is usually grown in HAT medium until hybridomas were established.

The limiting dilution method was used to select hybridomas that produced the antibody that binds to BCMA. First, it was made to be less than one cell per 96 well, and then clones proliferated from one cell were selected. The above process was repeated three times to select a hybridoma producing an antibody binding to BCMA.

The selected hybridoma was named 3G4 antibody (anti-hBCMA monoclonal antibody), and the amino acid sequence was analyzed. The sequence information for the heavy chain variable region and the light chain variable region of the antibody according to the sequencing results is shown in Table 1, and the underlined portions in Table 1 indicate the complementarity determining region (CDR).

TABLE 1

| Sequence information of 3G4 antibody | | |
| --- | --- | --- |
| 3G4 | sequence information | SEQ ID NO: |
| Heavy chain variable region CDR1 | GYTFSYV | SEQ ID NO: 1 |
| Heavy chain variable region CDR2 | IIPYNDGT | SEQ ID NO: 2 |
| Heavy chain variable region CDR3 | ARWNWDGYFDV | SEQ ID NO: 3 |
| Light chain variable region CDR1 | KSLLHSNGITY | SEQ ID NO: 4 |
| Light chain variable region CDR2 | QMS | SEQ ID NO: 5 |

TABLE 1-continued

| Sequence information of 3G4 antibody | | |
| --- | --- | --- |
| 3G4 | sequence information | SEQ ID NO: |
| Light chain variable region CDR3 | TQNLELPFT | SEQ ID NO: 6 |
| Amino acid sequence of heavy chain variable region | QVQLKESGPELVKPGASVKMSCKAS GYTFTSYV MHWVKQKPGQGLEWIGY IIPYNDGT KYNEKFKGKATLTSDKSSSTAYMELSSLTSEDSALYYC ARWNWDGYFDV WGAGTTVTVSS | SEQ ID NO: 7 |
| Amino acid sequence of light chain variable region | DIVMTQAAFSNPVTLGTSASISCRSS KSLLHSNGITY LYWYLQKPGQSPQLLIY QMS NLASGVPDRFSSSGSGTDFTLRISRVEAEDVGVFYC TQNLELPFTF GSGTKLEIK | SEQ ID NO: 8 |
| Nucleotide sequence of heavy chain variable region | CAGGTGCAGCTGAAGGAGTCTGGACCTGAGCTGG TAAAGCCTGGGGCTTCAGTGAAGATGTCCTGCAAG GCTTCTGGATACACATTCACTAGCTATGTTATGCAC TGGGTGAAGCAGAAGCCTGGGCAGGGCCTTGAGT GGATTGGATATATTATTCCTTACAATGATGGTACTA AGTACAATGAGAAGTTCAAAGGCAAGGCCACACTG ACTTCAGACAAATCCTCCAGTACAGCCTACATGGAG CTCAGCAGCCTGACCTCTGAGGACTCTGCGCTCTAT TACTGTGCAAGATGGAACTGGGACGGGTACTTCGA TGTCTGGGGCGCAGGGACCACGGTCACCGTCTCCT CA | SEQ ID NO: 9 |
| Nucleotide sequence of light chain variable region | GATATTGTGATGACGCAGGCTGCATTCTCCAATCCA GTCACTCTTGGAACATCAGCTTCCATCTCCTGCAGG TCTAGTAAGAGTCTCCTACATAGTAATGGCATCACT TATTTGTATTGGTATCTGCAGAAGCCAGGCCAGTCT CCTCAGCTCCTGATTTATCAGATGTCCAACCTTGCCT CAGGAGTCCCAGACAGGTTCAGTAGCAGTGGGTCA GGAACTGATTTCACACTGAGAATCAGCAGAGTGGA GGCTGAGGATGTGGGTGTTTTTTACTGTACTCAAA ATCTAGAACTTCCATTCACGTTCGGCTCGGGGACAA AGTTGGAAATAAAA | SEQ ID NO: 10 |

35

As shown in Table 1, it was confirmed that 3G4 antibody had a heavy chain variable region comprising a CDR1 region represented by the amino acid sequence of SEQ ID NO: 1 (GYTFTSYV), a CDR2 region represented by the amino acid sequence of SEQ ID NO: 2 (IIPYNDGT), and a CDR3 region represented by the amino acid sequence of SEQ ID NO: 3 (ARWNWDGYFDV); and a light chain variable comprising a CDR1 region represented by the amino acid sequence of SEQ ID NO: 4 (KSLLHSNGITY), a CDR2 region represented by the amino acid sequence of SEQ ID NO: 5 (QMS), and a CDR3 region represented by the amino acid sequence of SEQ ID NO: 6 (TQNLELPFT).

Specifically, it was confirmed that 3G4 antibody had a heavy chain variable region represented by the amino acid sequence of SEQ ID NO: 7 and a light chain variable region represented by the amino acid sequence of SEQ ID NO: 8; and the heavy chain variable region of 3G4 antibody was encoded by the nucleotide sequence of SEQ ID NO: 9 and the light chain variable region of the 3G4 antibody was encoded by the nucleotide sequence of SEQ ID NO: 10.

Example 2: Preparation of Humanized Antibody Based on 3G4 Antibody

A humanized antibody was prepared in which the 3G4 antibody selected in Example 1 was changed to a structure corresponding to a human.

Specifically, a humanized antibody was prepared from the mouse 3G4 antibody using a CDR-grafting method that replaces the CDRs of a human antibody with the CDRs of a mouse antibody that binds to BCMA with the germline sequence of a human antibody as a frame. The humanized antibody was named 3G4V2 and the amino acid sequence was analyzed. The sequence information on the heavy chain variable region and the light chain variable region of the antibody according to the sequencing results is shown in Table 2, and the underlined parts in Table 2 indicate the complementarity determining region (CDR).

TABLE 2

| Sequence information of 3G4V2 antibody | | |
| --- | --- | --- |
| 3G4V2 | sequence information | SEQ ID NO: |
| Heavy chain variable region CDR1 | GYTFSYV | SEQ ID NO: 1 |
| Heavy chain variable region CDR2 | IIPYNDGT | SEQ ID NO: 2 |

TABLE 2-continued

| Sequence information of 3G4V2 antibody | | |
|---|---|---|
| 3G4V2 | sequence information | SEQ ID NO: |
| Heavy chain variable region CDR3 | ARWNWDGYFDV | SEQ ID NO: 3 |
| Light chain variable region CDR1 | KSLLHSNGITY | SEQ ID NO: 4 |
| Light chain variable region CDR2 | QMS | SEQ ID NO: 5 |
| Light chain variable region CDR3 | TQNLELPFT | SEQ ID NO: 6 |
| Amino acid sequence of heavy chain variable region | QVQLVQSGAEVKKPGASVKVSCKAS GYTFTSYV MHWVRQAPGQRLEWIGY IIPYNDGT KYNEKFQGRVTLTSDKSSSTAYMELSSLRSEDTAV YYC ARWNWDGYFDV WGQGTTVTVSS | SEQ ID NO: 13 |
| Amino acid sequence of light chain variable region | DIVMTQSPLSLPVTPGEPASISCRSS KSLLHSNGITY LYWYLQKPGQSPQLLIY QMS NRASGVPDRFSSSGSGTDFTLKISRVEAEDVGVYYC TQNLELPFT FGQGTKLEIK | SEQ ID NO: 14 |
| Nucleotide sequence of heavy chain variable region | CAGGTGCAGCTGGTGCAGAGCGGCGCCGAGGTGA AGAAGCCGGGTGCTTCCGTGAAGGTGTCCTGTAAG GCCTCTGGCTACACCTTCACCAGCTACGTGATGCAT TGGGTCCGCCAGGCCCCCGGACAGCGCCTGGAGT GGATCGGTTACATCATCCCGTACAACGACGGCACT AAGTACAACGAGAAATTTCAGGGCCGAGTGACCCT GACCTCCGACAAATCCAGCTCGACCGCCTACATGG AGCTGTCTTCTCTGCGCTCGGAGGACACCGCGGTTT ATTACTGTGCTCGTTGGAACTGGGATGGCTATTTCG ACGTGTGGGGCCAGGGAACGACCGTCACCGTGTC GTCC | SEQ ID NO: 15 |
| Nucleotide sequence of light chain variable region | GACATCGTGATGACCCAGAGCCCTTTGTCTCTTCCT GTCACTCCGGGGGAGCCAGCTTCTATCTCATGCCG ATCTTCCAAGAGCCTGCTGCACTCAAATGGCATCAC CTACCTCTATTGGTACCTGCAGAAGCCCGGGCAATC CCCTCAGTTGCTCATCTATCAGATGTCTAACCGCGC CTCCGGTGTCCCCGACCGCTTCAGCTCCTCTGGCTC CGGCACCGACTTTACTCTGAAGATATCCCGCGTGG AGGCCGAAGATGTGGGCGTGTACTACTGCACTCAG AACCTGGAACTGCCCTTCACCTTCGGCCAGGGCAC CAAGCTGGAGATCAAG | SEQ ID NO: 16 |

As shown in Table 2, it was confirmed that 3G4V2 antibody had a heavy chain variable region represented by the amino acid sequence of SEQ ID NO: 13 and a light chain variable region represented by the amino acid sequence of SEQ ID NO: 14; and the heavy chain variable region of 3G4V2 antibody was encoded by the nucleotide sequence of SEQ ID NO: 15 and the light chain variable region of 3G4V2 antibody was encoded by the nucleotide sequence of SEQ ID NO: 16.

Example 3: Confirmation of BCMA Binding Ability of Anti-BCMA Antibody

In the present invention, it was confirmed whether the humanized anti-BCMA antibody, 3G4V2, prepared in Example 2 can specifically target BCMA.

First, to produce 3G4V2 antibody, the heavy chain variable region represented by the nucleotide sequence of SEQ ID NO: 15 was cloned into a heavy chain antibody expression vector of human antibody IgG1, and the light chain variable region represented by the nucleotide sequence of SEQ ID NO: 16 was cloned into was cloned into a light chain antibody expression vector of human antibody kappa; and each expression vector was co-transfected with CHO cells to produce an antibody. The produced antibody was purified using a Protein A column (Thermo Fisher, cat #20356).

Then, 1 mg each of the purified antibody was treated with A549 cells and hBCMA-expressing A549 cells, followed by treatment with a secondary antibody (Biolegend, cat #409304) specific for human IgG Fc. After reacting with the antibody, PE fluorescence of the secondary antibody was measured by flow cytometry.

As a result, as shown in FIG. 1, it was confirmed that binding to 3G4V2 was not confirmed in A549 cells not expressing hBCMA, but the binding capacity of A549 cells expressing hBCMA and 3G4V2 was increased to 60.1%.

Example 4: Construction of a Chimeric Antigen Receptor (CAR) Expression Vector Targeting BCMA In the present invention, a lentiviral vector (hBCMA-CAR lentivirus) expressing a chimeric antigen receptor (CAR) targeting BCMA containing 3G4V2 (humanized anti-BCMA antibody), prepared in Example 2, was prepared.

As shown in the schematic diagram of FIG. 3, CAR DNA composed of: EF1a promoter (SEQ ID NO: 20); a polynucleotide encoding a signal peptide (SEQ ID NO: 21); a polynucleotide encoding a BCMA-binding domain (SEQ ID NO: 18); a polynucleotide encoding a CD8 hinge region (SEQ ID NO: 22); a polynucleotide encoding a transmembrane domain (SEQ ID NO:23); a polynucleotide encoding 4-1BB (costimulatory domain) (SEQ ID NO: 24); a polynucleotide encoding CD3ζ intracellular signaling domain (SEQ ID NO: 25); and a polynucleotide encoding WPRE (SEQ ID NO: 26); was synthesized in vitro and inserted into a third-generation lentiviral vector.

Lenti-X 293T cells (co-After transfection) were co-infected with lentiviral vector and three vectors of pMDLg/pRRE (Addgene, cat ##12251), pMD2.G (Addgene, cat ##12259) & pRSV-Rev (Addgene, cat ##12253), and then hBCMA-CAR lentivirus was produced. For co-transfection, three vectors and Lenti-X 293T cells were incubated for 6 hours using Lipofectamine 3000 transfection kit (Invitrogen, cat #L3000-015) and Opti-MEM+GlutaMAX (gibco, cat #51985-034) media.

Example 5: Preparation of hBCMA-CAR-T Cell

In the present invention, the hBCMA-CAR lentiviral vector prepared in Example 4 was transformed into T cells, hBCMA-CAR-T cells (or 3G4V2-CAR-T cells) were prepared.

Specifically, as shown in FIG. 3, after separating peripheral blood mononuclear cells (PBMC) from blood, T cell activation beads (T cell activation beads; Miltenyl Biotec, cat #130-091-441) was used to activate T cells. hBCMA-CAR-T cells were prepared by transducing the activated T cells with the hBCMA-CAR lentivirus prepared in Example 4, and Lenti-boost-p was used to increase the transduction efficiency.

hBCMA peptide binding capacity of hBCMA-CAR-T cells was confirmed by flow cytometry. The hBCMA-CAR-T cells prepared above were reacted with FITC-hBCMA protein with anti-CD3, anti-CD4, and anti-CD8 antibodies, and then fluorescence intensity was measured using a FACS machine. In the course of the analysis, CD3 expressing cells were used as T cells, and the level of FITC expression in T cells was confirmed.

As a result, as shown in FIG. 4, it was confirmed that hBCMA-CAR-T cells expressing CD4 or CD8 binding to hBCMA increased as the hBCMA peptide increased. This means that the hBCMA-CAR-T cells prepared in the present invention effectively bind to BCMA.

Example 6: Confirmation of hBCMA-CAR-T Cell Activation by hBCMA Peptide

In the present invention, in order to check whether the hBCMA-CAR-T cells prepared in Example 5 are activated by the BCMA peptide, IFNγ and CD107a expression levels by hBCMA-CAR-T cells in the presence of target cells were confirmed.

As target cells, K562 cells that do not express BCMA (ATCC, cat #CCL-243) and H929 cells that express BCMA (ATCC, cat #CRL-9068) were used. After reacting hBCMA-CAR-T cells and target cells at a ratio of 2:1, 1:1. 0.5:1, 0:1 for a certain period of time, FACS measurement was performed by staining with surface & intra antibody (BCMA protein, INF-r, CD107a, CD3, CD4, CD8 staining). The levels of IFNγ and CD107a expressions of hBCMA-CAR-T reacted with target cells based on 0:1 (CAR-T only) were confirmed.

As a result, as shown in FIG. 5, it was confirmed that T cells were not activated in K562 cells not expressing BCMA, whereas T cells were activated in the presence of BCMA-expressing H929 cells to increase IFNγ expression.

Example 7: Confirmation of the Killing Effect of hBCMA-CAR-T Cells on BCMA-Expressing Cells In the present invention, the killing effect of target cells by hBCMA-CAR-T cells was confirmed.

As target cells, K562 cells that do not express BCMA, and RPMI8226 cells and H929 cells that express BCMA were used. After reacting hBCMA-CAR-T cells and target cells at a ratio of 1:4, 1:2, 1:1, 1:0.5 and 1:0.25, luminescence (CytoTox-Glo Cytotoxicity Assay, Promega, cat #G9291) was measured. From the measured value, the degree of cell death was calculated using Equation 1 below.

$$\% \text{ Cytotoxicity}=[(\text{Experimental}-\text{Effector Spontaneous}-\text{Target Spontaneous})/(\text{Target Maximum}-\text{Target Spontaneous})]\times 100 \qquad \text{[Equation 1]}$$

Experimental: Luminescence value derived from the medium of the target cell and CAR-T cell complex culture Effector Spontaneous: Luminescence value derived from the medium of CAR-T cells only Target Spontaneous: Luminescence value derived from the medium of target cells only Target Maximum: Luminescence value derived from 100% lysis of target cells (using Lysis Reagent)

As a result, as shown in FIG. 6, it was confirmed that hBCMA-CAR-T cells showed a specific killing effect on RPMI8226 cells and H929 cells expressing BCMA.

That is, chimeric antigen receptor and CAR-T cell targeting BCMA of the present invention can be usefully used as a composition for preventing or treating diseases related to B cell expression or BCMA expression.

INDUSTRIAL APPLICABILITY

It was confirmed that the antibody selected in the present invention specifically recognized BCMA-expressing cells, and the chimeric antigen receptor (CAR) and CAR-T cells targeting BCMA using the established antibody effectively bound BCMA. In addition, it was confirmed that the activation of CAR-T cells bound to BCMA was made.

In addition, since it was confirmed that the CAR-T cells of the present invention effectively killed BCMA-expressing cells, BCMA-specific antibody, BCMA-targeting chimeric antigen receptor, and CAR-T cells of the present invention can be usefully used for preventing or treating diseases related to B cell expression or BCMA expression.

The invention claimed is:

1. An antibody specifically binding to BCMA (B-cell maturation antigen) or fragment thereof, comprising:

a heavy chain variable region including a CDR1 region represented by the amino acid sequence of SEQ ID NO: 1, a CDR2 region represented by the amino acid sequence of SEQ ID NO: 2, and a CDR3 region represented by the amino acid sequence of SEQ ID NO: 3; and a light chain variable region including a CDR1 region represented by the amino acid sequence of SEQ ID NO: 4, a CDR2 region represented by the amino acid sequence of SEQ ID NO: 5, and a CDR3 region represented by the amino acid sequence of SEQ ID NO: 6.

2. The antibody specifically binding to BCMA or fragment thereof according to claim 1, wherein the antibody comprises a heavy chain variable region represented by the amino acid sequence of SEQ ID NO: 7 and a light chain variable region represented by the amino acid sequence of SEQ ID NO: 8; or a heavy chain variable region represented by the amino acid sequence of SEQ ID NO: 13 and a light chain variable region represented by the amino acid sequence of SEQ ID NO: 14.

3. A chimeric antigen receptor (CAR) comprising: a BCMA-binding domain; a transmembrane domain; a costimulatory domain; and an intracellular signal transduction domain, wherein the BCMA-binding domain includes an antibody specifically binding to BCMA or fragment thereof comprising:

a heavy chain variable region comprising a CDR1 region represented by the amino acid sequence of SEQ ID NO: 1, a CDR2 region represented by the amino acid sequence of SEQ ID NO: 2 and a CDR3 region represented by the amino acid sequence of SEQ ID NO: 3; and a light chain variable region comprising a CDR1 region represented by the amino acid sequence of SEQ ID NO:

4, a CDR2 region represented by the amino acid sequence of SEQ ID NO: 5, and a CDR3 region represented by the amino acid sequence of SEQ ID NO: 6.

4. The chimeric antigen receptor according to claim 3, wherein the transmembrane domain is a protein selected from the group consisting of CD8a, CD4, CD28, CD137, CD80, CD86, CD152 and PD1.

5. The chimeric antigen receptor according to claim 3, wherein the costimulatory domain is a protein selected from the group consisting of CD28, 4-1BB, OX-40 and ICOS.

6. The chimeric antigen receptor of claim 3, wherein the intracellular signal transduction domain is CD3ζ.

7. The chimeric antigen receptor according to claim 3, further comprising a hinge region between a C terminus of the BCMA-binding domain and an N terminus of the transmembrane domain.

8. A polynucleotide encoding the chimeric antigen receptor (CAR) of claim 3.

9. A vector comprising a polynucleotide encoding the chimeric antigen receptor (CAR) of claim 3.

10. The vector according to claim 9, wherein the vector is a plasmid, a retroviral vector, or a lentiviral.

11. An immune effector cell comprising a polynucleotide encoding the chimeric antigen receptor (CAR) of claim 3 or a vector comprising the polynucleotide.

12. The immune effector cell according to claim 11, wherein the immune effector cell is a T cell or a Natural Killer cell.

13. A pharmaceutical composition for preventing or treating a disease relating to BCMA expression comprising the immune effector cell of claim 11.

14. The pharmaceutical composition for preventing or treating a disease relating to BCMA expression of claim 13, wherein the disease relating to BCMA expression is multiple myeloma, hematologic cancer, non-Hodgkin's lymphoma, autoantibody-dependent autoimmune disease, systemic lupus erythematosus (SLE) or rheumatoid arthritis.

* * * * *